US012232961B2

(12) United States Patent
Franklin et al.

(10) Patent No.: US 12,232,961 B2
(45) Date of Patent: Feb. 25, 2025

(54) MITRAL VALVE SPACER DEVICE

(71) Applicant: Edwards Lifesciences Corporation, Irvine, CA (US)

(72) Inventors: Michael D. Franklin, Irvine, CA (US); Matthew T. Winston, Aliso Viejo, CA (US); Lauren R. Freschauf, Mission Viejo, CA (US); Eric Robert Dixon, Villa Park, CA (US); Yoon Hee Kwon, Mission Viejo, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 68 days.

(21) Appl. No.: 17/865,712

(22) Filed: Jul. 15, 2022

(65) Prior Publication Data

US 2022/0346946 A1 Nov. 3, 2022

Related U.S. Application Data

(63) Continuation of application No. 16/351,297, filed on Mar. 12, 2019, now Pat. No. 11,389,297.

(Continued)

(51) Int. Cl.
*A61F 2/24* (2006.01)

(52) U.S. Cl.
CPC ............ *A61F 2/246* (2013.01); *A61F 2/2463* (2013.01); *A61F 2/2409* (2013.01); *A61F 2/2412* (2013.01); *A61F 2/2436* (2013.01); *A61F 2/2445* (2013.01); *A61F 2/2457* (2013.01); *A61F 2/2466* (2013.01); *A61F 2210/0014* (2013.01); *A61F 2220/0008* (2013.01); *A61F 2220/0016* (2013.01); *A61F 2250/0003* (2013.01); *A61F 2250/0036* (2013.01); *A61F 2250/0069* (2013.01)

(58) Field of Classification Search
CPC ............................................. A61F 2/246–2463
See application file for complete search history.

(56) References Cited

U.S. PATENT DOCUMENTS

| 3,874,388 A | 4/1975 | King et al. |
| 4,340,091 A | 7/1982 | Skelton et al. |

(Continued)

FOREIGN PATENT DOCUMENTS

| CN | 1142351 A | 2/1997 |
| EP | 0098100 A2 | 1/1984 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.

(Continued)

*Primary Examiner* — Rebecca S Preston
(74) *Attorney, Agent, or Firm* — Anya Adams

(57) ABSTRACT

An implantable device includes an adjustable spacer and at least one anchor. The adjustable spacer is configured to be positioned between native heart valve leaflets to reduce regurgitation therebetween. The adjustable spacer can comprise a first side and a second side opposite the first side. Each side can be adjustable between a first width and a second width. Each side can be independently moved between the first width and the second width. The adjustable spacer can be made from a sponge material.

6 Claims, 14 Drawing Sheets

Related U.S. Application Data

(60) Provisional application No. 62/656,533, filed on Apr. 12, 2018.

(56) References Cited

U.S. PATENT DOCUMENTS

| | | |
|---|---|---|
| 4,506,669 A | 3/1985 | Blake, III |
| 4,590,937 A | 5/1986 | Deniega |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | St. Goar et al. |
| 6,719,767 B1 | 4/2004 | Kimblad |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,569,062 B1 | 8/2009 | Kuehn et al. |
| 7,682,369 B2 | 3/2010 | Seguin |
| 7,731,706 B2 | 6/2010 | Potter |
| 7,744,609 B2 | 6/2010 | Allen et al. |
| 7,748,389 B2 | 7/2010 | Salahieh et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,824,443 B2 | 11/2010 | Salahieh et al. |
| 7,981,123 B2 | 7/2011 | Seguin |
| 7,988,724 B2 | 8/2011 | Salahieh et al. |
| 8,052,750 B2 | 11/2011 | Tuval et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,133,239 B2 | 3/2012 | Oz et al. |
| 8,147,542 B2 | 4/2012 | Maisano et al. |
| 8,172,856 B2 | 5/2012 | Eigler et al. |
| 8,206,437 B2 | 6/2012 | Bonhoeffer et al. |
| 8,216,301 B2 | 7/2012 | Bonhoeffer et al. |
| 8,303,653 B2 | 11/2012 | Bonhoeffer et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,740,918 B2 | 6/2014 | Seguin |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,945,177 B2 | 2/2015 | Dell et al. |
| 9,034,032 B2 | 5/2015 | McLean et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,427,327 B2 | 8/2016 | Parrish |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |

(56) References Cited

U.S. PATENT DOCUMENTS

| | | |
|---|---|---|
| 10,076,415 B1 | 9/2018 | Metchik et al. |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,575,841 B1 | 3/2020 | Paulos |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0173251 A1 | 8/2006 | Govari et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Eliasen et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0288061 A1 | 11/2008 | Maurer et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0057192 A1 | 3/2010 | Celermajer |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022633 A1 | 1/2012 | Olson et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2013/0338763 A1* | 12/2013 | Rowe .................. A61F 2/2427 623/2.11 |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |

(56) References Cited

U.S. PATENT DOCUMENTS

| | | |
|---|---|---|
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008129 A1 | 1/2016 | Siegel |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0228246 A1* | 8/2016 | Zimmerman ......... A61F 2/2466 |
| 2016/0242906 A1 | 8/2016 | Morriss et al. |
| 2016/0287387 A1 | 10/2016 | Wei |
| 2016/0302811 A1 | 10/2016 | Rodriguez-Navarro et al. |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0325949 A1* | 11/2017 | Rodgers ................ A61F 2/2421 |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0078361 A1 | 3/2018 | Naor et al. |
| 2018/0092661 A1 | 4/2018 | Prabhu |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2019/0321166 A1 | 10/2019 | Freschauf et al. |
| 2020/0113683 A1 | 4/2020 | Dale et al. |
| 2020/0237512 A1 | 7/2020 | McCann et al. |
| 2020/0337842 A1 | 10/2020 | Metchik et al. |
| 2020/0352717 A1 | 11/2020 | Kheradvar et al. |
| 2021/0186698 A1 | 6/2021 | Abunassar et al. |
| 2021/0251757 A1 | 8/2021 | Siegel et al. |
| 2021/0259835 A1 | 8/2021 | Tyler, II et al. |
| 2021/0267781 A1 | 9/2021 | Metchik et al. |
| 2021/0338418 A1 | 11/2021 | Feld |
| 2021/0361416 A1 | 11/2021 | Stearns |
| 2021/0361428 A1 | 11/2021 | Dixon |
| 2021/0378818 A1 | 12/2021 | Manash et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0296248 A1 | 9/2022 | Abunassar et al. |
| 2022/0313433 A1 | 10/2022 | Ma et al. |
| 2023/0014540 A1 | 1/2023 | Metchik et al. |
| 2023/0149170 A1 | 5/2023 | Giese et al. |

(56) References Cited

U.S. PATENT DOCUMENTS

| | | | |
|---|---|---|---|
| 2023/0218291 | A1 | 7/2023 | Zarbatany et al. |
| 2023/0270549 | A1 | 8/2023 | Guidotti et al. |

FOREIGN PATENT DOCUMENTS

| | | | |
|---|---|---|---|
| FR | 2146050 | A5 | 2/1973 |
| FR | 2768324 | A1 | 3/1999 |
| WO | 2014064694 | A2 | 5/2014 |
| WO | 2017015632 | A1 | 1/2017 |
| WO | 2018013856 | A1 | 1/2018 |
| WO | 2018050200 | A1 | 3/2018 |
| WO | 2018050203 | A1 | 3/2018 |
| WO | 2018195015 | A1 | 10/2018 |
| WO | 2018195201 | A1 | 10/2018 |
| WO | 2018195215 | A2 | 10/2018 |
| WO | 2019139904 | A1 | 7/2019 |
| WO | 2020106705 | A1 | 5/2020 |
| WO | 2020106827 | A1 | 5/2020 |
| WO | 2020112622 | A1 | 6/2020 |
| WO | 2020167677 | A1 | 8/2020 |
| WO | 2020168081 | A1 | 8/2020 |
| WO | 2020172224 | A1 | 8/2020 |
| WO | 2020176410 | A1 | 9/2020 |
| WO | 2022006087 | A2 | 1/2022 |
| WO | 2022036209 | A1 | 2/2022 |
| WO | 2022051241 | A1 | 3/2022 |
| WO | 2022101817 | A2 | 5/2022 |
| WO | 2022140175 | A1 | 6/2022 |
| WO | 2022153131 | A1 | 7/2022 |
| WO | 2022155298 | A2 | 7/2022 |
| WO | 2022157592 | A1 | 7/2022 |
| WO | 2022212172 | A1 | 10/2022 |
| WO | 2023003755 | A1 | 1/2023 |
| WO | 2023004098 | A1 | 1/2023 |
| WO | 2023278663 | A2 | 1/2023 |
| WO | 2023288003 | A1 | 1/2023 |

OTHER PUBLICATIONS

Al-Khaja et al., "Eleven Years' Experience with Carpentier-Edwards Biological Valves in Relation to Survival and Complications", European Journal of Cardio-thoracic Surgery 3: pp. 305-311, 1989.

Almagor et al., "Balloon Expandable Stent Implantation in Stenotic Right Heart Valved Conduits", Journal of the American College of Cardiology, vol. 16, No. 6, pp. 1310-1314, Nov. 15, 1990.

Andersen, et al., "Transluminal implantation of artificial heart valves. Description of a new expandable aortic valve and initial results with implantation by catheter technique in closed chest pigs." European Heart Journal (1992), 13, 704-708.

Andersen, H.R. "History of Percutaneous Aortic Valve Prosthesis," Herz No. 34. pp. 343-346. 2009.

Batista RJ et al., "Partial left ventriculectomy to treat end-stage heart disease", Ann Thorac Surg., vol. 64, Issue—3, pp. 634-638, Sep. 1997.

Beall AC Jr. et al., "Clinical experience with a dacron velour-covered teflon-disc mitral-valve prosthesis", Ann Thorac Surg., vol. 5, Issue 5, pp. 402-410, May 1968.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, pp. 654-670, 1964.

Fucci et al., "Improved results with mitral valve repair using new surgical techniques", Eur J Cardiothorac Surg. 1995;Issue 9, vol. 11, pp. 621-626.

Inoune, M.D., Kanji, et al., Clinical Application of Transvenous Mitral Commissurotomy by a New Balloon Catheter,' The Journal of Thoracic and Cardiovascular Surgery 87:394-402, 1984.

Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue—3, pp. 240-245, Mar. 1998.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann et al., "Der Verschluß des Ductus Arteriosus Persistens Ohne Thorakotomie", Thoraxchirurgie Vaskulare Chirurgie, Band 15, Heft 2, Stuttgart, im Apr. 1967, pp. 199-203.

Praz et al., "Compassionate use of the Pascal transcatheter mitral valve repair system for patients with severe mitral regurgitation: a multicentre, prospective, observational, first-in-man study," Lancet, vol. 390, pp. 773-780, Aug. 19, 2017, Lancet, United States.

Reul RM et al., "Mitral valve reconstruction for mitral insufficiency", Prog Cardiovasc Dis., vol. 39, Issue—6, May-Jun. 1997.

Rosch, M.D., Josef, "The Birth, Early Years and Future of Interventional Radiology," J Vasc Interv Radiol 2003; 14:841-853.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology: 176. pp. 535-538, 1990.

Serruys et al., "Stenting of Coronary Arteries. Are we the Sorcerer's Apprentice?", European Heart Journal, 10, 774-782, pp. 37-45, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida et al., "Modifications of Gianturco Expandable Wire Stents", Technical Note, American Roentgen Ray Society, pp. 1185-1187, May 1988.

Umaña JP et al., Bow-tie' mitral valve repair: an adjuvant technique for ischemic mitral regurgitation', Ann Thorac Surg., vol. 66, Issue—6, pp. 1640-1646, Nov. 1998.

Urban, Philip MD, "Coronary Artery Stenting", Editions Medecine et Hygiene, Geneve, pp. 1-47, 1991.

Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.

Wheatley, David J., "Valve Prosthesis", Rob & Smith's Operative Surgery, pp. 415-424, 1986.

Grasso et al., "The Pascal transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi: 10.21037/jtd.2017.10.156, AME Publishing Company, Hong Kong, China.

* cited by examiner

MITRAL VALVE SPACER DEVICE

CROSS-REFERENCE TO RELATED APPLICATION

The present application is a continuation of U.S. application Ser. No. 16/351,297 filed on Mar. 12, 2019, published as U.S. Publication No. 2019/0314155 on Oct. 17, 2019, which claims the benefit of U.S. Provisional Application No. 62/656,533, filed on Apr. 12, 2018, which is incorporated by reference herein in its entirety.

FIELD

This disclosure relates generally to prosthetic devices and related methods for helping to seal native heart valves to prevent or reduce regurgitation therethrough, as well as devices and related methods for implanting such prosthetic devices.

BACKGROUND

The native heart valves (i.e., the aortic, pulmonary, tricuspid and mitral valves) serve critical functions in assuring the forward flow of an adequate supply of blood through the cardiovascular system. These heart valves can be damaged, and thus rendered less effective, by congenital malformations, inflammatory processes, infectious conditions, or disease. Such damage to the valves can result in serious cardiovascular compromise or death. For many years the definitive treatment for such damaged valves was surgical repair or replacement of the valve during open heart surgery. However, open heart surgeries are highly invasive and are prone to many complications. Therefore, elderly and frail patients with defective heart valves often went untreated. More recently, transvascular techniques have been developed for introducing and implanting prosthetic devices in a manner that is much less invasive than open heart surgery. One particular transvascular technique that is used for accessing the native mitral and aortic valves is the transseptal technique. The transseptal technique comprises inserting a catheter into the right femoral vein, up the inferior vena cava and into the right atrium. The septum is then punctured and the catheter passed into the left atrium where a procedure can be performed within the left side of the heart. Such transvascular techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is the most common form of valvular heart disease. Mitral regurgitation has different causes, such as leaflet prolapse, dysfunctional papillary muscles and/or stretching of the mitral valve annulus resulting from dilation of the left ventricle. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation.

Some prior techniques for treating mitral regurgitation include stitching portions of the native mitral valve leaflets directly to one another. Other prior techniques include the use of a spacer implanted between the native mitral valve leaflets. Despite these prior techniques, there is a continuing need for improved devices and methods for treating mitral valve regurgitation.

SUMMARY

Described herein are embodiments of prosthetic devices that are primarily intended to be implanted at one of the mitral, aortic, tricuspid, or pulmonary valve regions of a human heart, as well as apparatuses and methods for implanting the same. The prosthetic devices can be used to help restore and/or replace the functionality of a defective native valve.

An implantable prosthetic device can include one or more inflatable spacers and a frame having one or more anchors. The inflatable spacer can be configured to be disposed between native leaflets of a heart. The anchors can be coupled to the inflatable spacer and can be configured to secure the native leaflets against the inflatable spacer.

In some embodiments, the frame can further comprise a plurality of clasps. The clasps can be coupled to a respective anchor and configured to secure the native leaflets to the anchors. The clasps can be independently movable between an open configuration and a closed configuration.

In one representative embodiment, an implantable prosthetic device comprises an inflatable spacer having an interior cavity, the inflatable spacer being inflatable between an uninflated configuration and an inflated configuration, wherein in the inflated configuration the inflatable spacer is configured to be positioned between native heart valve leaflets to reduce regurgitation therebetween; and a frame comprising at least one anchor configured to be placed on one side of one of the native leaflets, and a clasp coupled to the anchor and configured to be placed on the other side of the one native leaflet, wherein the clasp is moveable between an open position and a closed position, wherein when in the closed position the clasp is configured to retain a portion of the one native leaflet to the anchor, and wherein the inflatable spacer is configured to be inflated from the uninflated configuration to the inflated configuration by filling the interior cavity of the inflatable spacer with an inflation medium or inflation media.

In some embodiments, the inflatable spacer is a balloon or other type of inflatable or fillable element (e.g., a cloth pocket). In such embodiments, the inflatable spacer can be inflatable between an uninflated configuration and a fully or partially inflated configuration. In certain embodiments, the inflatable spacer can be inflated by inflating an interior cavity of the inflatable spacer with an inflation medium or inflation media. The inflation medium can be a fluid and/or a non-fluid. Various fluids can be used such as saline solution, epoxy, blood, and/or other fluid configured for inflating. In some embodiments, the fluid can be a gaseous fluid, such as an inert gas (e.g., a gas that will not undergo chemical reactions, or at least undesired chemical reactions, with the body or components of the prosthetic spacer device under delivery conditions or after implantation). Suitable gasses can include nitrogen, carbon dioxide, helium, and argon, including mixtures thereof. Other gases, such as oxygen, may be included in mixtures of gases, such as air. The non-fluid can, for example, be a plurality of microbeads, a plurality of pellets, and/or other non-fluid medium configured for inflating. In some embodiments, both fluid and non-fluid media may be used in combination to inflate the inflatable spacer.

In some embodiments, the implantable prosthetic device can further comprise a source of the inflation medium. In some embodiments, the inflation medium can be a saline solution. In other embodiments, the inflatable spacer can be configured to receive blood to inflate the inflatable spacer from the uninflated configuration to the inflated configuration.

In some embodiments, the inflatable spacer can comprise a plurality of inflatable members each having an interior cavity. The plurality of inflatable members can be distinct structures or can be a single structure having a plurality of chambers. The inflatable members can be individually moveable between a fully or partially inflated configuration and an uninflated configuration. The inflatable members can be inflated in a symmetrical configuration or in an asymmetrical configuration.

In some embodiments, the inflatable spacer can comprise first and second inflatable members. In such embodiments, the asymmetrical configuration can comprise inflating, for example, the first inflatable member to the fully inflated configuration and leaving the second inflatable member in the uninflated configuration. The symmetrical configuration can comprise, for example, inflating both the first and second inflatable members to the fully inflated configuration.

In some embodiments, the inflatable spacer can have a substantially cylindrical shape (i.e. having a round cross-sectional shape taken in a plane perpendicular to an axis extending from the proximal end portion to the distal end portion of the prosthetic spacer device). In other embodiments, the inflatable spacer can be substantially rectangular, annular, semi-circular, or have another shape configured to create a surface against which the native leaflets can coapt. In some embodiments, the inflatable spacer can be a non-uniform shape configured to fill a space between improperly functioning native leaflets that do not coapt completely. In some embodiments, the inflatable spacer can have tapered end portions.

In some embodiments, the inflatable spacer can comprise one or more inflation valves through which inflation media can enter and/or exit the interior cavity of the inflatable spacer and/or the interior cavities of the inflatable members and either inflate or deflate the inflatable spacer and/or the inflatable members.

In some embodiments, the inflation valve can be a slit valve. The slit valve can have a flexible annular seal through which an inflation shaft of the delivery system can extend. When the inflation shaft is removed from the flexible annular seal the seal can bias closed, preventing any inflation medium from exiting and/or entering the interior cavity of the inflatable spacer.

In other embodiments, the inflation valve can be a check valve. The check valve can be configured to prevent inflation medium from entering the interior cavity of the inflatable spacer if the pressure external to the check valve is greater than the opening (or "cracking") pressure of the check valve. If the external pressure is greater than the cracking pressure of the check valve, the valve will open and allow media to enter the interior cavity of the inflatable spacer.

In other embodiments, the inflation valve may be a ball valve, a diaphragm valve, a swing valve, an in-line valve, or other type of valve.

In some embodiments, the inflatable spacer can be formed from various materials, including polymers such as nylon, polyesters, polypropylenes, polytetrafluoroethylene, expanded polytetrafluoroethylene, silicone, urethane, and poly-carbonate-based and/or polyether-based thermoplastic polyurethanes (TPU).

In some embodiments, the interior cavity of the inflatable spacer can contain a matrix material. For example, the interior cavity can contain a gel foam, a sponge, a clotting agent, hemostatic matrices, and/or spun collagen hemostatic granules. In such embodiments, the matrix material may expand and/or solidify when contacted by the material used to expand the inflatable spacer.

In some embodiments, the implantable prosthetic device can further comprise a stretchable cover covering an external surface of the inflatable spacer. The stretchable cover can comprise a material configured to promote tissue ingrowth. In other embodiments, in lieu of or in addition to the material configured to promote tissue ingrowth the stretchable cover can comprise a material configured to delay or prevent tissue ingrowth. In some embodiments, the cover can be elastic. In other embodiments, the inflatable spacer can be non-elastic and the cover can stretch in at least one direction upon inflation of one of the inflatable members.

In some embodiments, the inflatable spacer of the implantable prosthetic device can comprise a longitudinal axis extending from an upstream end to a downstream end of the spacer and the spacer can be configured form an asymmetric shape with respect to the longitudinal axis when the spacer is at least partially inflated.

In another representative embodiment, an implantable prosthetic device can comprise an inflatable spacer configured to be positioned between native heart valve leaflets to reduce regurgitation therebetween, the spacer comprising a plurality of inflatable members each having an interior cavity, each inflatable member being inflatable between an uninflated configuration and an inflated configuration, and at least one anchor configured to anchor the inflatable spacer relative to the native leaflet, wherein each inflatable member can be independently inflated to a respective inflated configuration.

In some embodiments, the plurality of inflatable members can comprise a first inflatable member and a second inflatable member. The first and second inflatable members can be different sizes and/or shapes when fully inflated.

In some embodiments, the inflatable spacer can form an asymmetric shape when the inflatable members are inflated with different amounts of an inflation medium.

In some embodiments, the plurality of inflatable members can comprise first and second inflatable members that extend radially outwardly from a central longitudinal axis of the spacer on diametrically opposed sides of the longitudinal axis. In some embodiments, each inflatable member can comprise first and second, opposed major surfaces that are configured to coapt with the native leaflets when the spacer is implanted between the leaflets, each inflatable member having a width measured from the first major surface to the second major surface, and each inflatable member is configured to increase in width as it inflated.

In some embodiments, the inflatable spacer can comprise first and second media pathways. The first media pathway can be adapted to receive a pressurized inflation medium and allow the medium to flow into the first inflatable member, and the second media pathway can be adapted to receive the pressurized inflation medium and allow the medium to flow into the second inflatable member.

In some embodiments, the anchor of the inflatable prosthetic device can comprise at least two anchors configured to anchor onto the native leaflets.

In another representative embodiment, an implantable prosthetic device comprises an inflatable spacer, a plurality of anchors, and a plurality of clasps. The inflatable spacer is configured to be disposed between native leaflets of a heart. The anchors are coupled to the inflatable spacer and configured to anchor the inflatable spacer relative to the native leaflet. The clasps are configured to secure the native leaflets to the anchors and have fixed end portions and free end portions. The fixed end portions are coupled to the anchors. The free end portions have barbs. The free end portions are pivotable relative to the fixed end portions between an open configuration and a closed configuration. The free end portions are axially movable in the open configuration from a first position in which the barbs engage tissue of the native leaflets to a second position in which the barbs disengage the tissue of the native leaflets.

In another representative embodiment, an assembly comprises an implantable prosthetic spacer device and a delivery apparatus. The implantable prosthetic device has an inflatable spacer and a frame comprising a plurality of anchors, a plurality of clasps, a first collar, and a second collar. First end portions of the anchors are coupled to a first end portion of the inflatable spacer, and second end portions of the anchors are coupled to the first collar. The second collar is coupled to a second end portion of the inflatable spacer, and the clasps are coupled to the anchors. The delivery apparatus has a first shaft, a second shaft, and a plurality of clasp control members. The clasp control members are releasably coupled to the clasps of the prosthetic device. Actuating the clasp control members moves the clasps between an open configuration and a closed configuration.

In some embodiments, the delivery apparatus further comprises one or more inflation shafts for inflating the inflatable spacer and/or inflatable members. The inflation shafts are configured to releasably couple the inflatable spacer allowing medium used to inflate the inflatable spacer to enter the interior cavity thereof.

In some embodiments, the delivery apparatus further comprises a media source, and the inflation shafts can be releasably coupled to the media source. The media source can be configured to supply and/or retrieve a medium to inflate and/or deflate the inflatable spacer.

In some embodiments, the delivery apparatus is configured such that moving the first shaft and the second shaft relative to each other moves the prosthetic device between a first configuration, in which anchors are in a radially compressed, and a second configuration, in which the anchors are in a radially expanded, axially compressed configuration and at least partially overlap the inflatable spacer to capture native leaflets between the anchors and the inflatable spacer.

In some embodiments, the delivery apparatus further comprises a clasp control mechanism, and the clasp control members are releasably coupled to the clasp control mechanism. The clasp control mechanism is configured such that the clasp control members can be actuated either simultaneously or separately.

In another representative embodiment, an assembly comprises a prosthetic spacer device and a delivery apparatus. The delivery apparatus comprises an outer shaft, an actuation shaft, and a plurality of tethers. The outer shaft has a first lumen and a plurality of second lumens disposed radially outwardly from the first lumen. The actuation shaft extends through the first lumen. The actuation shaft is axially movable relative the outer shaft and releasably coupled to the prosthetic device. The tethers extend through the second lumens and are releasably coupled to the prosthetic device. Tensioning the tethers moves the implantable prosthetic device and the outer shaft toward each other. Slackening the tethers allows the implantable prosthetic device and the outer shaft to be spaced apart from each other.

In some embodiments, each of the tethers is disposed in two of the second lumens that are circumferentially offset by approximately 180 degrees.

In some embodiments, the prosthetic spacer device further comprises a plurality of clasps. The clasps are coupled to a respective anchor and are configured to secure the native leaflets to the anchors. The clasps are movable between an open configuration and a closed configuration. The outer shaft of the delivery apparatus further comprises a plurality of third lumens disposed radially outwardly from the first lumen. The delivery apparatus further comprises a plurality of control members extending through the third lumens and releasably coupled to the clasps of the prosthetic device. Tensioning the control members moves the clasps to the open configuration. Slackening the control members allows the clasps to move to the closed configuration.

In some embodiments, each of the control members is disposed in two of the third lumens that are circumferentially offset by approximately 180 degrees.

In another representative embodiment, an assembly comprises an implantable prosthetic spacer device and a delivery apparatus. The implantable prosthetic spacer device has an inflatable spacer comprising a plurality of inflatable members, a plurality of anchors, a plurality of clasps, a first collar, and a second collar. The first end portions of the anchors are coupled to a first end portion of the inflatable spacer, and second end portions of the anchors are coupled to the first collar. The second collar is coupled to a second end portion of the inflatable spacer, and the clasps are coupled to the anchors and are independently movable between an open configuration and a closed configuration. The delivery apparatus has a first shaft, a second shaft, a plurality of tethers, and a plurality of clasp control members. The first shaft is releasably coupled to the first collar of the prosthetic device by the tethers, the second shaft is releasably coupled to the second collar of the prosthetic device, and the clasp control members are releasably coupled to the clasps of the prosthetic device. Actuating the clasp control members moves the clasps between an open configuration and a closed configuration. Tensioning the tethers moves the prosthetic device and the first shaft toward each other, and slackening the tethers allows the prosthetic device and the first shaft to be spaced from each other.

In a representative embodiment, a method for implanting a prosthetic spacer device to improve coaptation of native heart valve leaflets can comprise advancing a delivery apparatus and an implantable prosthetic device into a body of a patient, the implantable prosthetic device comprising an inflatable spacer comprising at least first and second inflatable members. Positioning the inflatable spacer between the native heart valve leaflets, and at least partially inflating at least the first inflatable member with an inflation medium so that the spacer assumes an asymmetric configuration against which the native leaflets can coapt.

In some embodiments, the method can further comprise anchoring the prosthetic device against tissue in the heart with an anchor of the prosthetic device so as to support the spacer between the native leaflets.

In some embodiments, the asymmetric configuration of the spacer can be asymmetric with respect to a central longitudinal axis of the spacer that extends from an upstream end to a downstream end of the spacer. In some embodiments, the asymmetric configuration can be asymmetric with respect to a lateral axis of the spacer. In some embodiments, the method can further comprise inflating the second inflatable member to create a symmetric configuration against which the native leaflets can coapt.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the invention will become more apparent from the following detailed description, which proceeds with reference to the accompanying figures.

DETAILED DESCRIPTION

General Considerations

Figure 1:
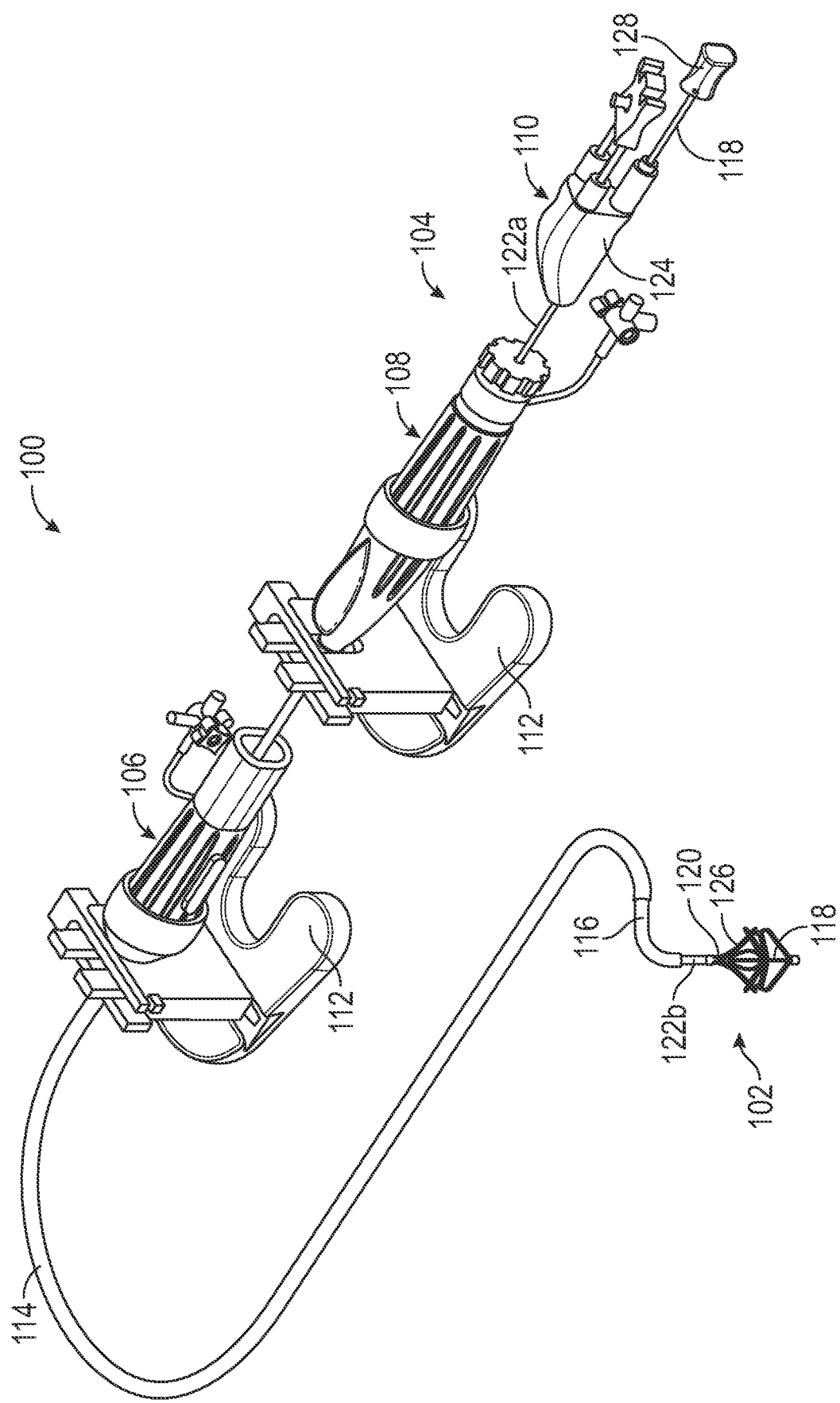
FIG. 1 illustrates an exemplary embodiment of a delivery assembly comprising a delivery apparatus and a prosthetic spacer device.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

As used herein, the term "approximately" means the listed value and any value that is within 10% of the listed value. For example, "approximately 100 degrees" means any value between 90-110 degrees, inclusive.

Exemplary Embodiments

Described herein are embodiments of prosthetic spacer devices that are primarily intended to be implanted at one of the mitral, aortic, tricuspid, or pulmonary valve regions of a human heart, as well as apparatuses and methods for implanting the same. The prosthetic spacer devices can be used to help restore and/or replace the functionality of a defective native valve.

A prosthetic spacer device can be coupled to a delivery apparatus to form a delivery assembly. The delivery apparatus can be used to percutaneously deliver, position, and/or secure the prosthetic spacer device within a patient's native heart valve region.

FIG. 1 shows an exemplary embodiment of a delivery assembly 100 and its components. The delivery assembly 100 can comprise a prosthetic spacer device 102 and a delivery apparatus 104. The delivery apparatus 104 can comprise a plurality of catheters and catheter stabilizers. For example, in the illustrated embodiment, the delivery apparatus 104 includes a first catheter 106, a second catheter 108, a third catheter 110, and catheter stabilizers 112. The second catheter 108 extends coaxially through the first catheter 106, and the third catheter 110 extends coaxially through the first and second catheters 106, 108. The prosthetic spacer device 102 can be releasably coupled to a distal end portion of the third catheter 110 of the delivery apparatus 104, as further described below.

In the illustrated embodiment, the delivery apparatus 104 is configured, for example, for implanting the prosthetic spacer device 102 in a native mitral valve via a transseptal delivery approach. In other embodiments, the delivery apparatus 104 can be configured for implanting the prosthetic spacer device 102 in aortic, tricuspid, or pulmonary valve regions of a human heart. Also, the delivery apparatus 104 can be configured for various delivery methods, including transseptal, transaortic, transventricular, etc.

The first and second catheters 106, 108 can be used, for example, to access an implantation location (e.g., a native mitral valve region of a heart) and/or to position the third catheter 110 at the implantation location.

The first and second catheters 106, 108 can comprise first and second sheaths 114, 116, respectively. The first and second catheters 106, 108 can be configured such that the sheaths 114, 116 are steerable. Additional details regarding the first catheter 104 can be found, for example, in U.S. Patent Application Publication No. 2018/0126124, which is incorporated by reference herein. Additional details regarding the second catheter 106 can be found, for example, in U.S. Pat. No. 10,076,638, which is incorporated by reference herein.

Referring still to FIG. 1, the delivery apparatus 104 can also include the third catheter 110, as mentioned above. The third catheter 110 can be used, for example, to deliver, manipulate, position, and/or deploy the prosthetic spacer device 102 at the implantation location. The third catheter 110 can comprise an inner or actuation shaft 118, a coupler 120, an outer shaft 122, a handle 124, and clasp control members 126. A proximal end portion 122a of the outer shaft 122 can be coupled to and extend distally from the handle 124. A distal end portion 122b of the outer shaft 122 can be coupled to the coupler 120, which can be releasably coupled to the proximal end portion of the prosthetic spacer device 102. A proximal end portion 118a of the actuation shaft 118 can be coupled to actuation knob 128. The actuation shaft 118 can extend distally from the knob 128, through the handle 124, through the outer shaft 122, and through the coupler 120. The actuation shaft 118 can be moveable (e.g., axially and/or rotationally) relative to the outer shaft 122 and the handle 124. The distal end portion of the actuation shaft 118 can be releasably coupled to a distal end portion of the prosthetic spacer device 102. The clasp control members 126 can extend through and be axially moveable relative to the handle 124 and the outer shaft 122. The clasp control members 126 can also be axially moveable relative to the actuation shaft 118. The clasp control member 126 can be releasably coupled to the prosthetic spacer device 102.

In a particular embodiment, the delivery apparatus 104 can include one or more inflation shafts (not shown). The inflation shafts can be releasably coupled to and in fluidic communication with the prosthetic spacer device 102. In this manner, an inflation medium (e.g., a saline solution) can flow from a media source (e.g., a reservoir), through the inflation shafts, and to the prosthetic spacer device 102 to inflate the prosthetic spacer device 102, and/or can flow from the prosthetic spacer device 102, through the inflation shafts, and to the media source to deflate the prosthetic spacer device 102. In some embodiments, the inflation shafts can extend through and/or be integrally formed with the third catheter 110.

The components of the delivery apparatus 104 can be formed from various materials, including metals and polymers. For example, in one particular embodiment, the proximal end portion 122a of the outer shaft 122 can comprise stainless steel and the distal and intermediate portions can comprise PEBA (e.g., PEBAX®). The outer shaft 122 can also comprise an outer covering or coating such as a polymer that is reflowed over the portions.

The delivery apparatus 104 can be releasably coupled to the prosthetic spacer device 102. In some embodiments, such as those shown in FIG. 1, the coupler 120 can be used to couple the prosthetic spacer device 102 to a portion of the outer shaft 122. In other embodiments, the prosthetic spacer device 102 can be coupled to the delivery apparatus 104 by a plurality of tethers. The coupler and tethers are described in more detail below.

In general, a prosthetic spacer device comprises a frame having one or more anchors and an inflatable spacer. In some embodiments, the inflatable spacer can comprise a plurality of inflatable members, as described in more detail below. In certain embodiments, the frame can further comprise at least one clasp and at least one collar. In some embodiments, the frame can comprise a plurality of anchors and/or a plurality of clasps.

Figure 2:
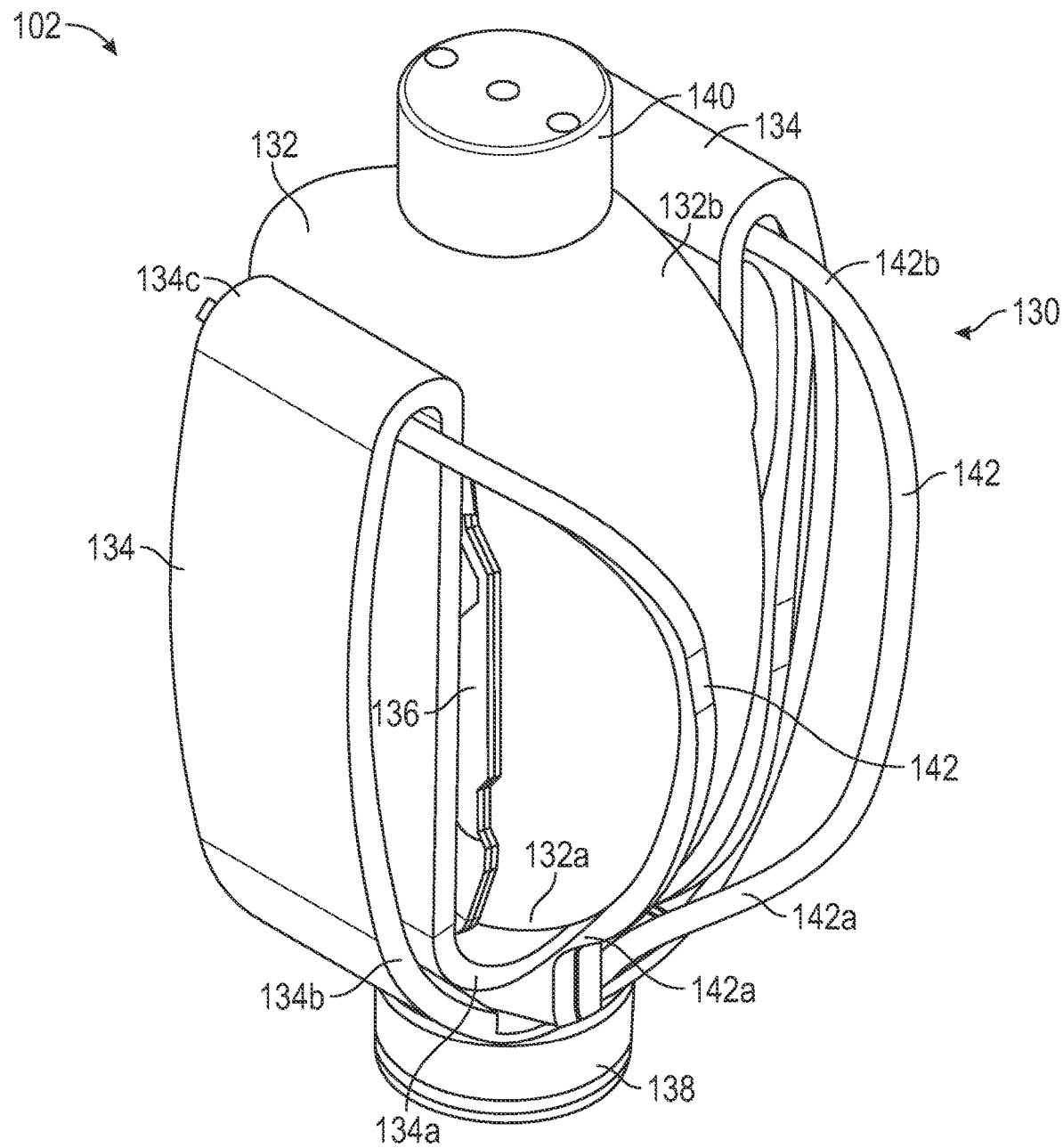
FIG. 2 illustrates an exemplary embodiment of a prosthetic spacer device.
Figure 3:
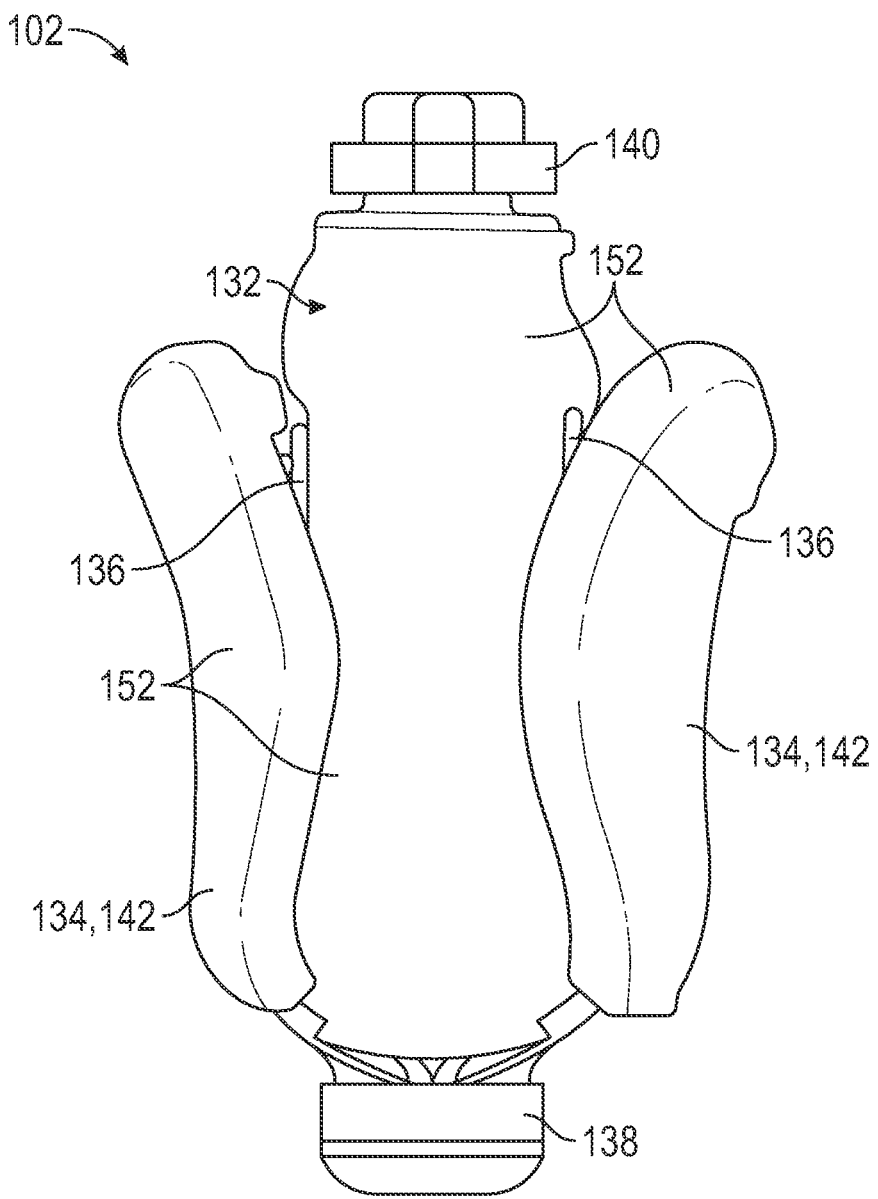
FIG. 3 is a side elevation view of the prosthetic spacer device of FIG. 2, showing a cover thereon.

FIGS. 1-3 show an exemplary embodiment of a prosthetic spacer device 102 and its components. Referring now to FIG. 2, the prosthetic spacer device 102 can comprise a frame 130 coupled to an inflatable spacer 132.

Figure 6:
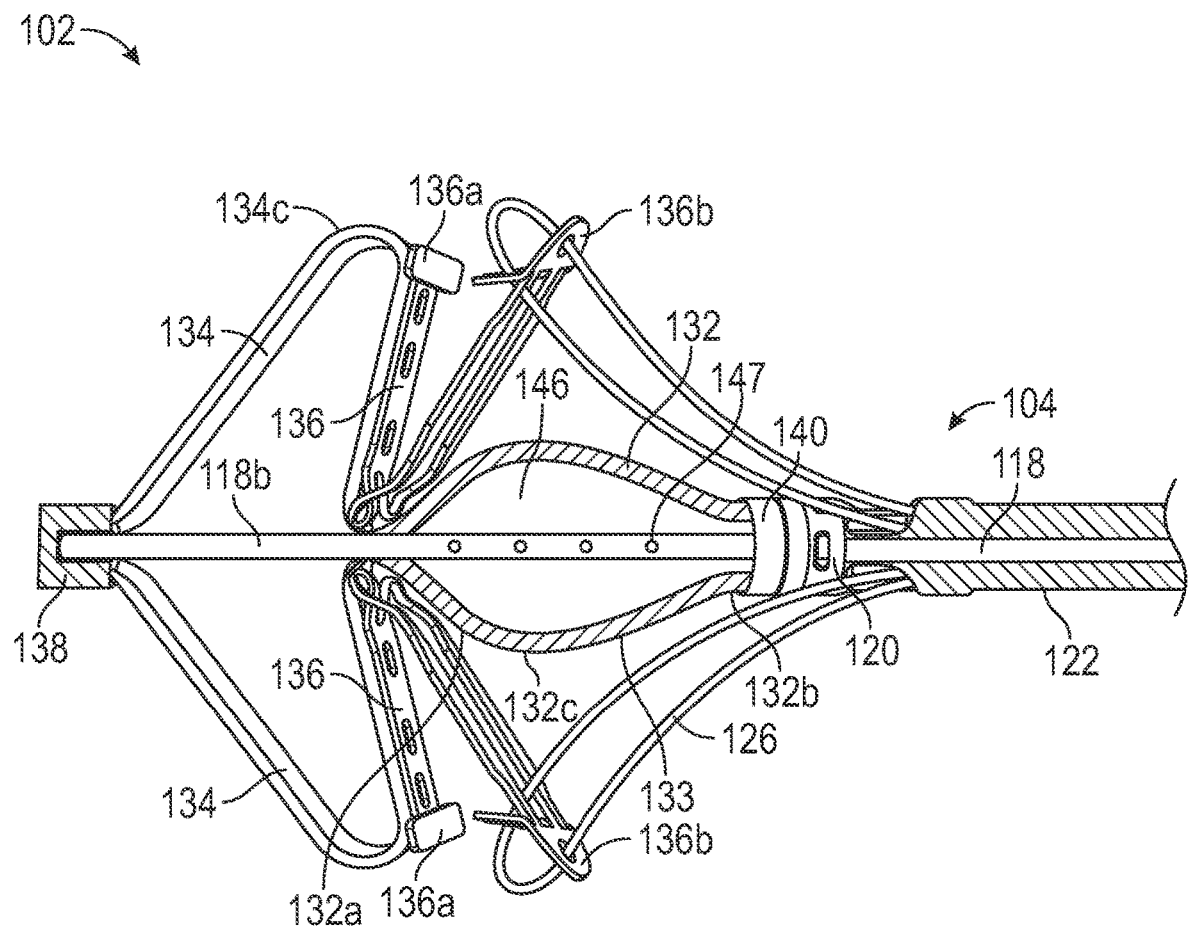
FIG. 6 is a partial cross-section of the prosthetic spacer device of FIG. 2.

Referring to FIG. 6, the frame 130 can include one or more anchors 134 (e.g., two in the illustrated embodiments). The frame 130 can, in some embodiments, further comprise a plurality of clasps 136 (e.g., two in the illustrated embodiment), a first collar 138 located at a distal end of the prosthetic spacer device 102, and a second collar 140 located at a proximal end of the prosthetic spacer device 102. In some embodiments, the frame 130 can omit one or more of these elements, for example, the clasps 136 and/or the first and second collars 138, 140.

Figure 13:
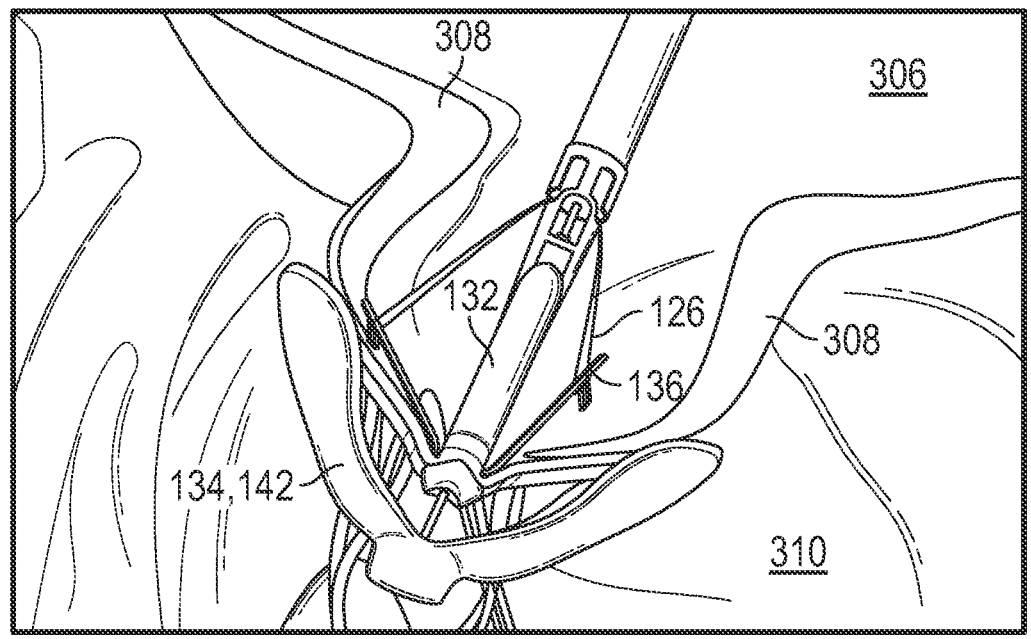

The anchors 134 and/or the clasps 136 of the frame 130 can be configured to secure the prosthetic spacer device 102 to one or more of the native leaflets such that the inflatable spacer 132 is positioned between the native leaflets (see, e.g., FIG. 13). The anchors 134 can be configured to be positioned behind (e.g., on the ventricular side) the native leaflets when implanted such that the anchors 134 anchor the inflatable spacer 132 relative to the native leaflets (see, e.g., FIG. 14). In some embodiments, the anchors 134 and the inflatable spacer 132 can be configured such that the native leaflets are captured between the anchors 132 and the inflatable spacer 132.

The anchors 134 can be configured to move between various configurations by axially moving the first collar 138 and thus the anchors 134 relative to the inflatable spacer 132 along a longitudinal axis extending between first and second end portions 132a, 132b of the inflatable spacer 132. For example, the anchors 134 can be positioned in a substantially straight, unfolded configuration wherein the joint portions 134c of the anchors are adjacent the longitudinal axis of the inflatable spacer 132 (e.g., FIG. 11). Alternately, the anchors 134 can be positioned in a fully folded configuration (e.g., FIG. 9) by moving the first collar 138 toward the inflatable spacer 132.

In certain embodiments, the clasps 136 are attached to the anchors 134. The clasps 136 can be configured to capture and secure a native leaflet to the anchor 134, as shown for example in FIG. 13. In certain embodiments, the clasps 136 are independently or separately actuatable such that each of the native leaflets can be captured sequentially.

Referring again to FIG. 6, the clasps 136 can comprise attachment portions 136a and arm portions 136b. The attachment portions 136a can be coupled to the anchors 134 in various ways such as with sutures, adhesive, fasteners, welding, and/or means for coupling. The arm portions 136b can pivot between open and closed configurations. In the open configuration, the attachment portions 136a and the arm portions 136b pivot away from each other such that native leaflets can be positioned between the attachment portions 136a and the arm portions 136b. In the closed configuration, the attachment portions 136a and the arm portions 136b pivot toward each other, thereby clamping the native leaflets between the attachment portions 136a and the arm portions 136b.

In some embodiments, the clasps 136 can be formed from a shape memory material such as Nitinol, stainless steel, and/or shape memory polymers. In certain embodiments, the clasps 136 can be formed by laser-cutting a flat sheet of material (e.g., Nitinol) and then shape-setting the clasp 136.

Referring again to FIG. 2, in some embodiments, the prosthetic spacer device 102 can further comprise anchor extension members 142 (e.g., two in FIG. 2). The anchor extension members 142 can be configured as loops with first or fixed end portions 142a coupled to and extending from the first collar 138, and second or free end portions 142b disposed opposite the fixed end portions 142a. The anchor extension members 142 can be configured to extend circumferentially farther around the inflatable spacer 132 than the anchors 134.

The anchor extension members 142 can further be configured such that free end portions 142b are disposed axially adjacent a joint portion 134c of the anchors 134 and radially between first and second portions 134a, 134b of the anchors 134 when the prosthetic spacer device 102 is in a folded configuration (e.g., FIG. 2).

Configuring the anchor extension members 142 in this manner provides increased surface area compared to the anchors 134 alone. This can, for example, make it easier to capture and secure the native leaflets. The increased surface area can also distribute the clamping force of the anchors 134 and anchor extension members 142 against the native leaflets over a relatively larger surface of the native leaflets in order to further protect the native leaflet tissue.

In some embodiments, the second collar 140 and/or the inflatable spacer 132 can comprise a hemostatic sealing member (not shown) configured to reduce or prevent blood from flowing through the second collar 140 and/or into the inflatable spacers 132. For example, in some embodiments, the sealing member can comprise a plurality of flexible flaps. The flaps can be configured to pivot from a sealed configuration to an open configuration to allow a delivery apparatus to extend through the second collar 140. When the delivery apparatus is removed, the flaps can be configured to return to the sealed configuration from the open configuration.

Figure 7:
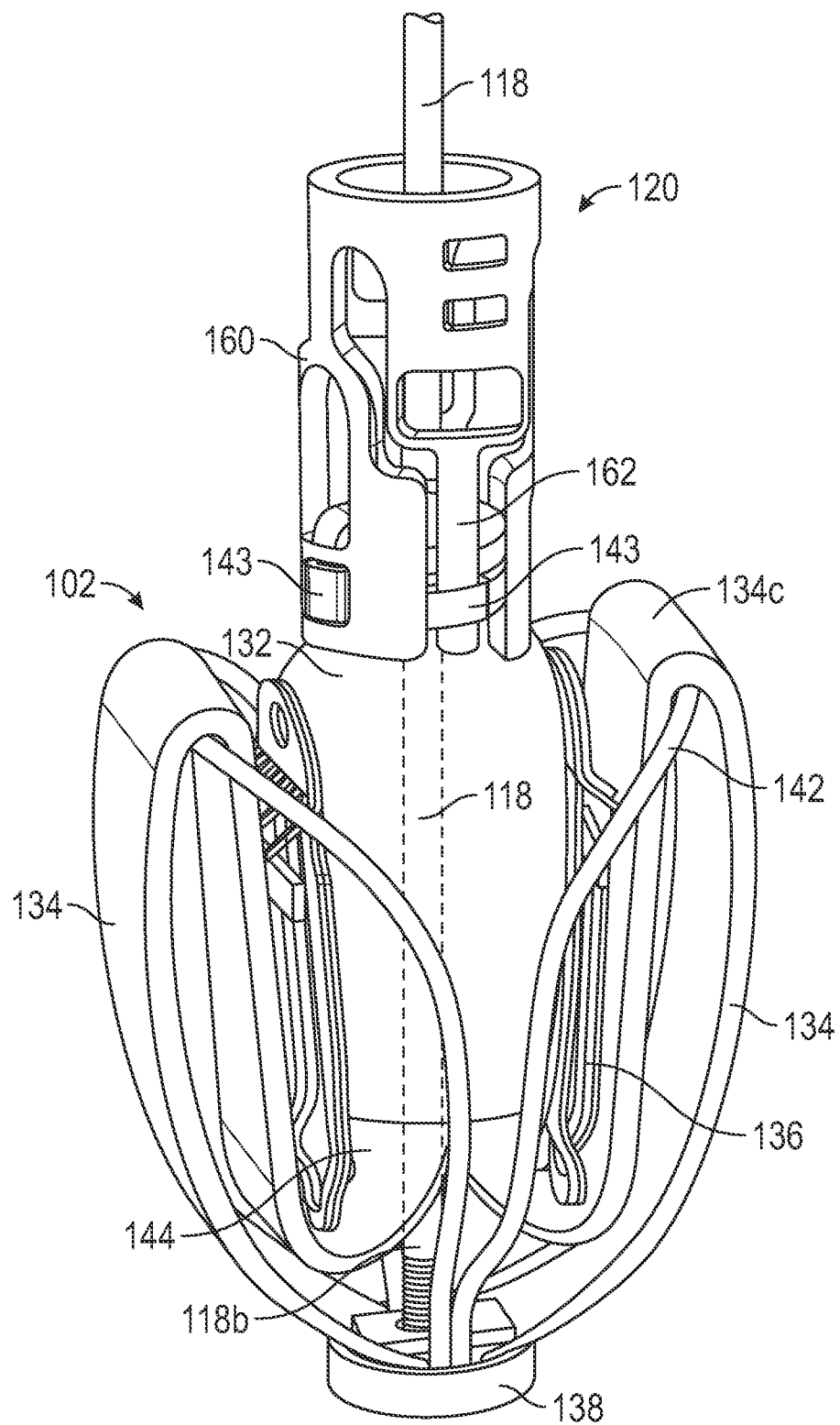
FIG. 7 is a perspective view of a distal end portion of the delivery assembly of FIG. 1 showing the prosthetic spacer device releasably coupled to the delivery apparatus.
Figure 8:
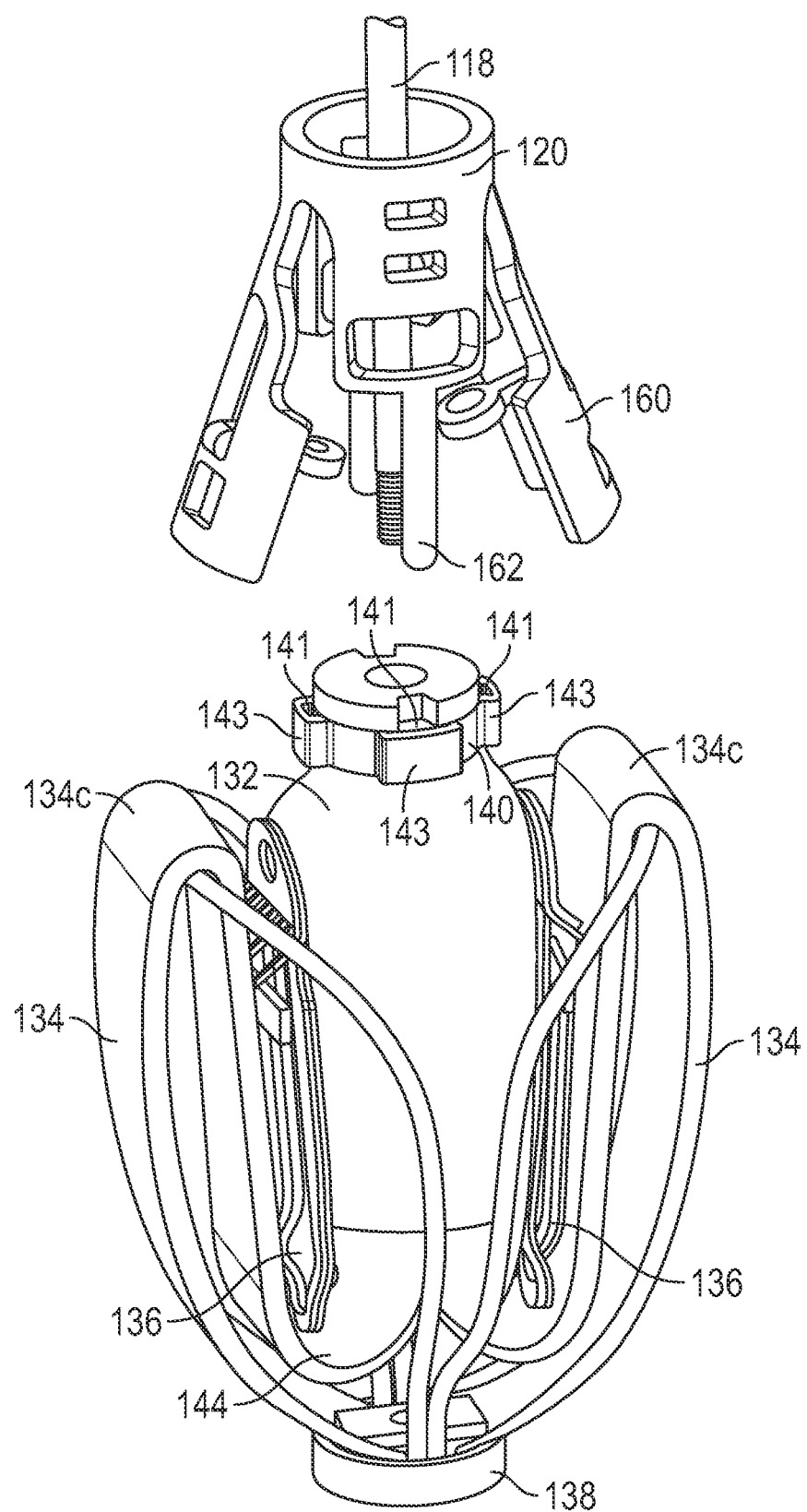
FIG. 8 is a perspective view of the distal end portion of the delivery assembly of FIG. 1 showing the prosthetic spacer device released from the delivery apparatus.

In other embodiments, for example, as shown in FIGS. 7 and 8, the prosthetic device may comprise a third collar 144 (see e.g., FIG. 7) coupled to the distal end portion of the inflatable spacer 132. The anchors 134 may be coupled to the third collar 144 by integrally forming the third collar 144 and the anchors 134 as a single, unitary component (see e.g., FIGS. 7 and 8). In other embodiments, the third collar 144 and the anchors 134 can be coupled together by welding, fasteners, adhesive, and/or other means for coupling. In yet other embodiments, the third collar 144 can be omitted, and the anchors 134 can be directly coupled to a first end portion 132a of the inflatable spacer 132.

Referring again to FIG. 2, the frame 130 can be coupled to the inflatable spacer 132. The frame 130 can be coupled to the inflatable spacer 132 by fasteners, adhesive, sutures, and/or other means of coupling. In some embodiments, first end portions 134a of the anchors 134 can be coupled to and extend from the first end portion 132a of the inflatable spacer 132, and second end portions 134b of the anchors 134 can be coupled to the first collar 138. The second collar 140 can be coupled to a second end portion 132b of the inflatable spacer 132.

The inflatable spacer 132 can be configured to be positioned within a native valve orifice to fill a space between improperly functioning native leaflets that do not naturally coapt completely. As such, the inflatable spacer 132 can help create a more effective seal between the native leaflets and prevent or minimize regurgitation (e.g., mitral regurgitation). In some embodiments, the inflatable spacer 132 can comprise a shape and/or structure that that allows the native leaflets to close around the sides of the inflatable spacer 132 to block retrograde blood flow (e.g., blood flowing from the left ventricle back into the left atrium during ventricular systole).

The inflatable spacer 132 can be inflated and deflated between an uninflated configuration and an inflated configuration. The uninflated configuration can be used, for example, to reduce the radial profile of the prosthetic spacer device 102 when the prosthetic spacer device 102 is advanced through a patient's vasculature to an implantation location. The inflated configuration can be used, for example, to block regurgitation through native valve leaflets.

In certain embodiments, the inflatable spacer 132 can be inflated by introducing an inflation medium such as an inflation fluid and/or a non-fluid. An inflation fluid can be, for example, saline solution, a curable epoxy, blood, and/or other material configured for inflating. Conversely, the spacer 132 can be deflated by removing fluid from the spacer. In some embodiments, if the material from which the inflatable spacer 132 is formed is sufficiently robust, the inflation fluid can be a gaseous fluid, such as an inert gas (e.g., a gas that will not undergo chemical reactions, or at least undesired chemical reactions, with the body or components of the prosthetic spacer device under delivery conditions or after implantation). Suitable gasses can include nitrogen, carbon dioxide, helium, and argon, including mixtures thereof. Other gases, such as oxygen, may be included in mixtures of gases, such as air. The non-fluid can be, for example, a plurality of pellets and/or microbeads. Embodiments using a non-fluid to inflate the inflatable spacer 132 can, for example, allow for a relatively simple seal to be used because the seal does not need to maintain fluid pressure of an inflation fluid and/or hemostasis to retain the inflatable spacer 132 in the inflated configuration. Combinations of fluids (e.g., saline solution and curable epoxy), combinations of non-fluids (e.g., microbeads and pellets), and/or combinations of fluids and non-fluids (e.g., saline solution and microbeads) can be used to inflate the inflatable spacer 132.

In some embodiments, the inflatable spacer 132 can be impervious to blood. In other embodiments, the inflatable spacer 132 can be partially or fully permeable to blood to fill an internal cavity or chamber 146 (see FIG. 6) of the inflatable spacer 132 with blood.

In some embodiments, the inflatable spacer 132 can be a balloon or other type of inflatable or fillable element. The inflatable spacer 132 can be constructed from any suitable material. In some embodiments, the materials are flexible, conformable, and/or stretchable materials that can expand as increasing amounts of media are placed inside a hollow interior portion of the inflatable spacer. Suitable materials include polymers such as nylon, polyesters, polypropylenes, polytetrafluoroethylene (PTFE), expanded polytetrafluoroethylene, silicone, urethane, poly-carbonate-based and/or polyether-based thermoplastic polyurethanes (TPU).

In some embodiments, the inflatable spacer 132 can be constructed of cloth or fabric such as polyethylene terephthalate (PET), velour, and/or other suitable cloth or fabric. In some instances, the cloth or fabric can form a pocket that is configured to receive a non-fluid inflation media (e.g., microbeads and pellets), which fills and thus expands the inflatable spacer 132.

In particular embodiments, the spacer 132 is formed from a single layer 133 of material (e.g., a polymer layer) that is shaped to define the internal cavity 146. In some embodiments, the layer 133 is substantially non-elastic so that the layer 133 does not stretch when filled with the inflation medium. In other embodiments, the layer 133 is elastic and can stretch when inflated with the inflation medium. In alternative embodiments, the spacer 132 can comprise multiple layers that form a laminate structure.

Use of an inflatable spacer 132 allows the prosthetic spacer device 102 to be inserted with a minimal profile (e.g., diameter) and to be inflated once the prosthetic spacer device is in a selected position (e.g., within the heart). Use of an inflatable spacer can, for example, create a better sealing surface for the native leaflets and/or reduce mitral regurgitation.

The extent to which the inflatable spacer 132 is inflated can vary. For example, the inflatable spacer 132 can be inflated from the uninflated configuration to a diameter of 2-20 mm or, in some embodiments, 5-15 mm. In one particular embodiment, the inflatable spacer 132 can be inflated to 5 mm, 7.5 mm, 10 mm, and/or 12 mm. This adjustable inflatability can, for example, allow the inflatable spacer 132 to be adjusted within a patient's body during the implantation procedure to accommodate a specific patient's anatomical variability. This in turn reduces the need to remove and/or replace an improperly sized prosthetic spacer device during the delivery procedure for a larger or smaller device. It also provides a more precise fit because the spacer can be adjusted to a range of sizes. For example, the inflatable spacer 132 of the prosthetic spacer device 102 can be inflated to 8 mm; whereas other devices may only be available in 5 mm or 10 mm sizes, which are either undersized or oversized for an 8 mm regurgitation orifice. In some embodiments, the size of the spacer 132 can be adjusted by adding or removing inflation medium in a subsequent procedure. For example, the spacer 132 can be further inflated in a subsequent procedure if the regurgitation orifice increases over the patient's lifetime.

The adjustable nature of the inflatable spacer 132 also mitigates the need for using multiple prosthetic devices at a single regurgitation location. Using only one prosthetic spacer device can, for example, make the implantation procedure relatively easier, reduce the risk of device displacement, and/or reduce undesirable interference with antegrade flow through the valve.

In certain embodiments configured for implantation in a native mitral valve, the inflatable spacer 132 can have an atrial or upper end portion positioned in or adjacent the left atrium of the heart, a ventricular or lower end portion positioned in or adjacent the left ventricle of the heart, and a center portion that extends between the native mitral valve leaflets.

Referring to FIG. 6, the inflatable spacer 132 can have an interior cavity 146, through which the actuation shaft 118 can extend. In other embodiments, the inflatable spacer 132 can include an inner shaft extending through the cavity 146 from the first end 132a to the second end 132b of the cavity with the shaft defining an inner lumen through which the actuation shaft 118 can extend.

As shown in FIGS. 1-3, in some embodiments the inflatable spacer 132 can have a symmetrical shape (e.g., ovular, cylindrical, rectangular, etc.) about a lateral axis and/or a longitudinal axis of the prosthetic spacer device 102 when fully or partially inflated. In other embodiments, the inflatable spacer 132 can have an asymmetrical shape about the lateral and/or longitudinal axes of the prosthetic spacer device 102 when fully or partially inflated. In a partially inflated state, the inflatable spacer 132 can be partially filled with an inflation medium, thus allowing the shape of the inflatable spacer 132 to change in situ, such as when the native mitral leaflets coapt around the inflatable spacer.

The inflatable spacer 132 can have various shapes. In some embodiments, the inflatable spacer 132 can have a cylindrical shape (i.e. having a round cross-sectional shape taken in a plane perpendicular to the longitudinal axis of the prosthetic spacer device 102). In other embodiments, the inflatable spacer 132 can be substantially rectangular, elliptical, annular, semi-circular, or have another shape configured to create a surface against which the native leaflets can coapt. In some embodiments, the inflatable spacer 132 can be a non-uniform shape configured to fill a space between improperly functioning native leaflets that do not coapt completely. In some embodiments, the inflatable spacer can have tapered end portions and/or tapered side portions. In particular embodiments, when the spacer 132 is inflated, the spacer has a variable width or diameter along its length with a maximum diameter or width at an intermediate portion 132c between the first and second ends 132a, 132b of the spacer. The spacer tapers from the intermediate portion 132c to the first and second ends, which have diameters or widths that are smaller than the diameter of the intermediate portion.

Referring to FIGS. 4A-5B, there is shown a representative embodiment of a prosthetic spacer device 102 for improving coaptation of native or artificial heart valve leaflets. The prosthetic spacer device 102 can include an inflatable spacer 132 comprising a plurality of inflatable members 200 (e.g., 2-4 members), each having an interior cavity or chamber that can be filled with an inflation medium. The inflatable members 200 can be distinct structures or can be a single structure having a plurality of chambers. The inflatable members 200 can be coupled to the frame 130, and in some embodiments, the inflatable members can be coupled together. To better illustrate the inflatable members, the anchor extension members 142 are not shown in FIGS. 4A-5B.

For example, in FIGS. 4A-5B, the prosthetic spacer device 102 has an inflatable spacer comprising two inflatable members 200a, 200b. The first inflatable member 200a and the second inflatable member 200b can be part of a unitary inflatable body or structure, such as a balloon. For example, a unitary body can be formed from a single polymer layer or a laminate structure and then fluidly separated into multiple chambers, such as by bonding (e.g., welding or adhering, for example, using an adhesive such as an epoxy) opposing sides of the body to each other. In other embodiments, the first inflatable member 200a and the second inflatable member 200b can comprise separate inflatable bodies or structures (e.g., separate balloons), and may be appropriately secured to one another (e.g., by mechanical means and/or use of an adhesive and/or other type of bonding mechanism). Although the spacer device in the illustrated configuration comprises two inflatable members, in other embodiments, the spacer device can have any number of inflatable members, such as three, four, five, six, or more inflatable members.

Whether the inflatable members are different portions of the same inflatable structure or separate inflatable structures, in certain embodiments the inflatable members can be in fluid communication with each other, whereas in other embodiments, the inflatable members can be fluidly separated or sealed off from each other. When the inflatable members are in fluid communication with each other, they can be shaped or configured to be inflated to different volumes to achieve an overall asymmetrical shape, as further discussed below.

In some embodiments, the spacer 132 defines a longitudinally extending opening or a lumen that extends from the collar 140 to the collar 138 between the inflatable members 200, through which the actuation shaft 118 can extend. In some embodiments, the inflatable spacers 200 may be coupled to centrally disposed shaft or sleeve 206 (FIG. 4A), through which the actuation shaft 118 can extend. The shaft 206 can be coupled to the inflatable spacers 200 in various ways such as with fasteners, sutures, adhesive, and/or other means for coupling. The shaft 206 can extend axially from one collar 138 to the other collar 140.

Figure 4A:
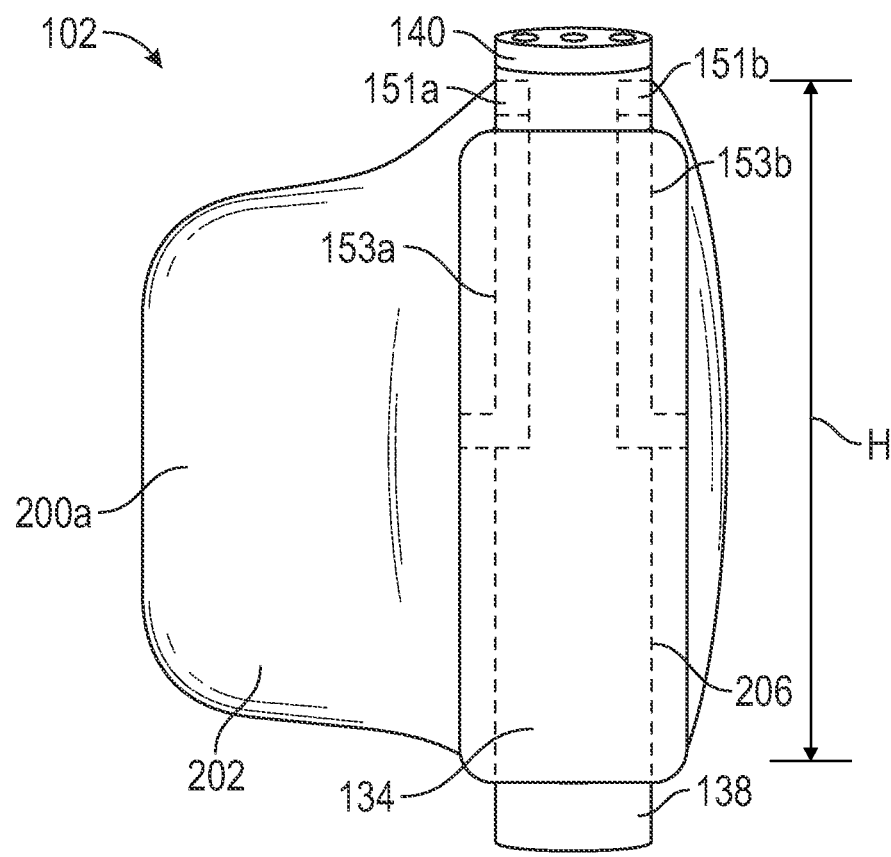
FIG. 4A is a side elevation view of an exemplary embodiment of a prosthetic spacer device in an asymmetrically inflated configuration.
Figure 4B:
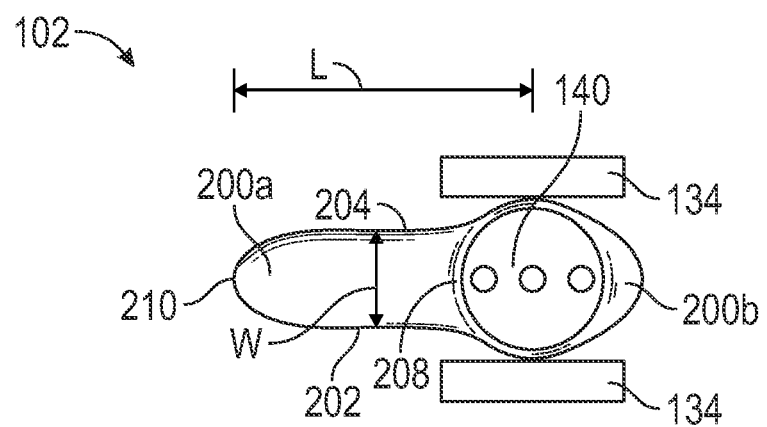
FIG. 4B is a plan view of the prosthetic spacer device of FIG. 4A.
Figure 5A:
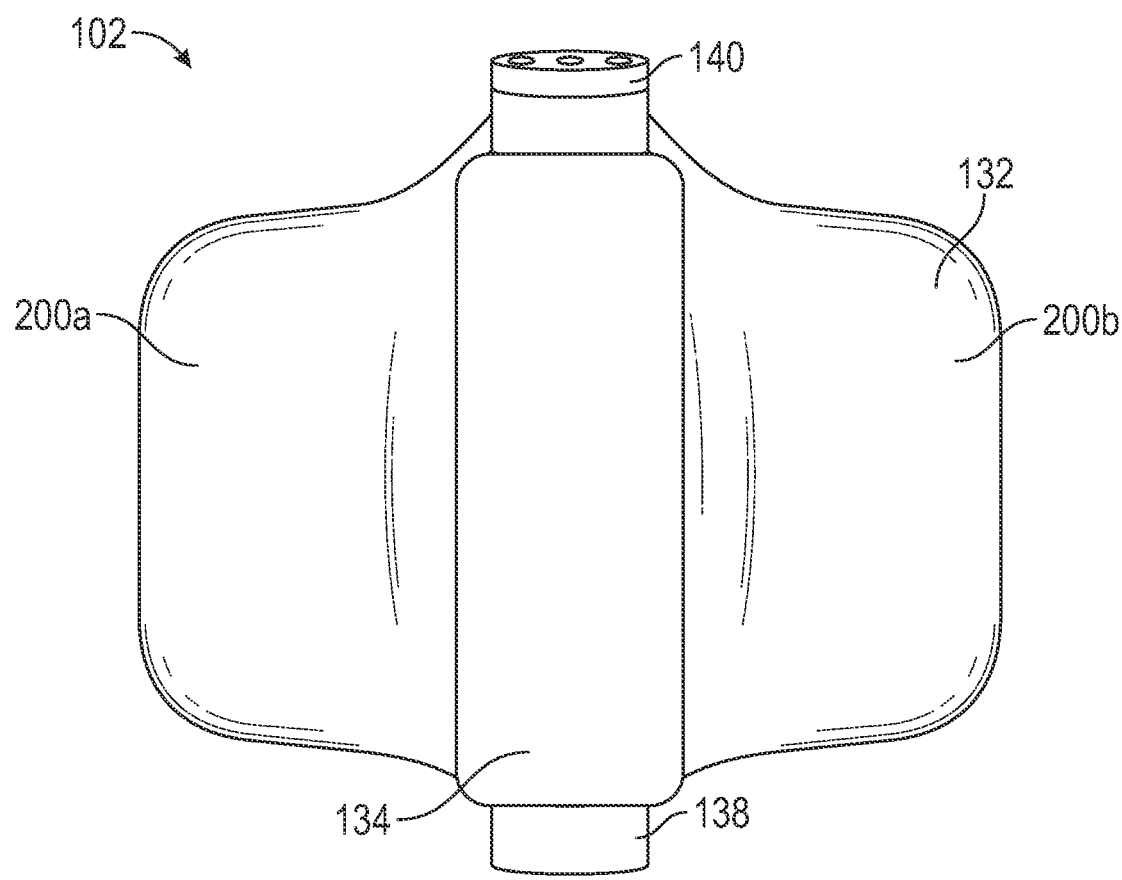
FIG. 5A is a side elevation view of the prosthetic spacer device of FIG. 4A in a symmetrically inflated configuration.
Figure 5B:
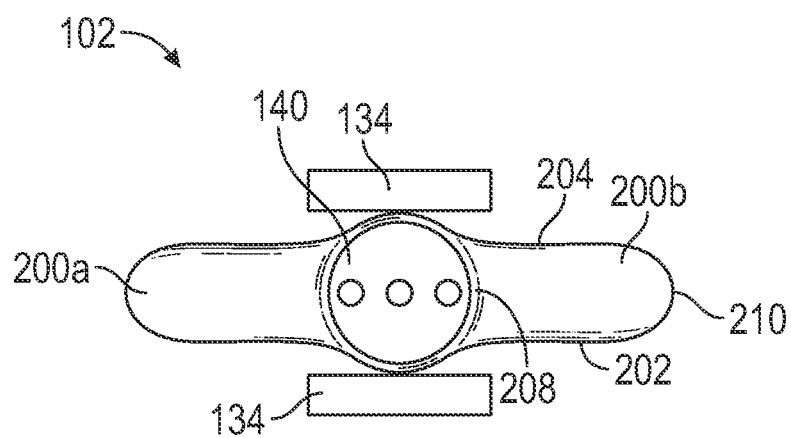
FIG. 5B is a plan view of the prosthetic spacer device of FIG. 5A.

Referring still to FIGS. 4A-5B, the inflatable members 200 can extend laterally from opposite sides of the shaft 206 and collars 138, 140 when inflated and can be flush or at least substantially flush with the shaft 206 when uninflated. For example, in FIGS. 4A-4B, the inflatable member 200a is inflated and extends from the shaft 206 in a length dimension L (measured from a center or midpoint of the prosthetic spacer device 102 to an outer edge 210 of the inflatable member 200) and in a width dimension W (measured between opposing major surfaces 202, 204), and the inflatable member 200b is uninflated and is substantially flush with the shaft 200b. In FIGS. 5A-5B, both inflatable members 200a, 200b are inflated. The inflatable members 200a, 200b can be configured such that the extent to which each of the inflatable members 200a, 200b extends in length L, width W, and/or height H can vary in the inflated and uninflated configurations from that which is shown in FIGS. 4A-5B. For example, one or more of the inflatable members can extend to a greater or lesser extent when inflated than the inflatable member 200a as depicted FIGS. 4A-4B, and one or more of the inflatable members can extend to a greater or lesser extend when uninflated than the inflatable member 200b as depicted in FIGS. 4A-4B.

The inflatable members 200 can be partially inflated, fully inflated, and/or deflated independently of one another. In some embodiments, each of the inflatable members 200 can be deflated and/or partially or fully inflated independently of one another to create various symmetrical or asymmetrical configurations. FIGS. 4A and 4B show an exemplary asymmetrical configuration that is achieved by inflating the first inflatable member 200a to an inflated configuration and maintaining the second inflatable member 200b in an uninflated configuration.

FIGS. 5A-5B shows the same device in an exemplary symmetrical configuration that is achieved by inflating both the first and second inflatable members 200a, 200b to their inflated configurations. Though FIGS. 4-5 show both the first and second inflatable members 200a, 200b as having substantially the same size and shape, in other embodiments, the first inflatable member 200a can have a shape and/or configuration that is different from the second inflatable member 200b. This can, for example, provide additional adjustability of the prosthetic spacer device 102.

Referring to FIGS. 4A and 4B, when fully inflated, each member 200a, 200b can have a height H (measured from the upstream end to the downstream end of the member), a length L (measured from a center or midpoint of the prosthetic spacer device 102 to an outer edge of the member in the radial direction), and a width W (measured between the two major surfaces 202, 204 of the member). In embodiments where one or more of the dimensions H, L, and/or W are not constant, the dimensions can be nominal or average values or can be measured at a particular location. For example, if the width W is less at an outer edge than at one or more other locations, the width W can be measured at a midpoint of the length (i.e., L/2).

In some embodiments, each member 200a, 200b has the same size and shape when fully inflated. In some embodiments, each member 200a, 200b has the same shape when fully inflated but one or more of the dimensions H, L, or W of one of the members differs from the other member. For example, one of the members can be longer, wider and/or taller than the other member. In still other embodiments, the members 200a, 200b can have different shapes when fully inflated. For example, one of the members can have the shape shown in FIGS. 4A-5B, while other members can have a different shape, such as circular or elliptical in cross-section.

In embodiments configured for implantation in a native mitral valve, the height H can generally correspond to superior/inferior anatomical directions, the length L can correspond to medial/lateral anatomical directions, and the width W can correspond to anterior/posterior anatomical directions. In embodiments configured for implantation in other locations, the height H, the length L, and the width W can correspond to other anatomical directions.

In particular embodiments, the height H can be in the range of about 2.5 mm to about 20 mm, and more particularly in the range of about 5 mm to about 15 mm, with 11 mm being a specific example; the length L can be in the range of about 1 mm to about 20 mm, and more particularly in the range of about 2.5 mm to about 15 mm, with 10 mm being a specific example; and the width W can be in the range of about 1 mm to about 15 mm, and more particularly in the range of about 2 mm to about 10 mm, with 5 mm being a specific example.

In some embodiments, the length L can be greater than the width W when the inflatable members 200 are inflated.

The symmetrical and asymmetrical inflatable spacer shapes and configurations allow variability in the positioning of the prosthetic spacer device 102 along the native leaflets. Based on in vivo echo imagery, a physician can decide whether symmetrical or asymmetrical inflation of the prosthetic spacer device 102 would be more beneficial to a patient. In patients where anatomical considerations limit the possible attachment locations, the ability to asymmetrically inflate an inflatable spacer (e.g., by inflating one or more inflatable members 200) can reduce the need for additional implants, and thus reduce the associated risks thereof. For example, a physician can attach the prosthetic spacer device 102 to the native leaflets at a location that is offset (e.g., toward the A1/P1 location of the native leaflets when implanted in the mitral valve) from the location of the regurgitation (e.g., at the A2/P2 location of the native mitral valve leaflets) and asymmetrically inflate the inflatable spacer such that the inflatable spacer blocks the regurgitation in the A2/P2 location but does not occlude the A1/P1 location. Further, the adjustable nature of the inflatable spacers allows for repositioning and/or readjusting the prosthetic spacer device 102 during implantation, as described in more detail below. This can also allow the prosthetic spacer device 102 to be adjusted after the initial implantation (e.g., during a subsequent procedure).

Inflating the inflatable members 200a, 200b to different sizes creates asymmetry with respect to the longitudinal axis of the prosthetic device. In other embodiments, the prosthetic device 102 can include inflatable members arranged to provide asymmetry with respect to a lateral axis (an axis parallel to the length L) and perpendicular to the longitudinal axis (an axis parallel to the height H) in lieu of or in addition to having longitudinal asymmetry. For example, in some embodiments, the prosthetic device can include an inflatable member at an upstream end of the device and a separate inflatable member at a downstream end of the device. The inflatable members at the upstream and downstream ends can be inflated to different volumes to achieve asymmetry with respect to a lateral axis bisecting the prosthetic device midway between the upstream and downstream ends of the device.

As mentioned above, the spacer device can be releasably coupled to the delivery apparatus 104. The delivery apparatus 104 can, in some embodiments, be used to inflate and/or deflate the inflatable spacers.

In some embodiments, the second collar 140 can facilitate inflation of the prosthetic spacer device 102 by the delivery apparatus 104. Referring to FIG. 6, the second collar can include a central opening configured to slidably receive, for example, actuation shaft 118 which may be used to deliver an inflation medium to inflate the inflatable spacer 132 during an implantation procedure. For example, the proximal end portion of the actuation shaft 118 can be fluidly connected to a media source and can comprise one or more side openings 147 spaced along the length of the portion of the shaft located within the internal cavity 146 of the spacer. A pressurized inflation medium from the media source can flow through a lumen of the actuation shaft 118 through the openings 147 and into the inflatable spacer 132.

In such embodiments, the second collar 140 can comprise a sealing member (not shown), such as a hemostatic sealing member. In a specific example, the sealing member can be a slit valve formed from an elastomeric (e.g., rubber) or other self-sealing material defining the central opening for receiving the actuation shaft 118. The slit valve can be housed within an outer ring of the collar 140. When formed of an elastomeric material, the central bore of the slit valve can expand to accommodate passage of the actuation shaft 118 (or a separate inflation shaft of the delivery apparatus) into the prosthetic device 102. When inserted through the central bore, the slit valve can seal around the outer surface of the shaft. When the shaft is withdrawn from the prosthetic device 102, the central bore of the slit valve closes under the resiliency of the elastomeric material.

In embodiments wherein the inflatable spacer comprises a plurality of inflatable members (e.g., two), the actuation shaft can, for example, be formed with first and second lumina that separately deliver an inflation medium to the first and second inflatable members, respectively. The first lumen can extend through the actuation shaft from its proximal end to a first side opening formed in the shaft at a location within the first inflatable member. The second lumen can extend through the actuation shaft from its proximal end to a side opening formed in the shaft at a location with the second inflatable member. In this manner, the inflation medium can be delivered to the first and second inflatable members through separate media pathways, concurrently or consecutively. Instead of separate lumens, the inflation medium can be delivered to the first and second inflatable members via separate conduits or tubes extending through the collar or apart from the collar.

Referring now to FIG. 4A, in some embodiments, the second collar 140, and/or another portion of the prosthetic spacer device 102 can comprise an inflation valve 151 which can be used to control the flow of the inflation medium into the inflatable members 200a, 200b. The inflation valve 151 can be a slit valve, a check valve, and/or another type of valve configured to regulate or control inflation and/or deflation of the inflatable member(s).

In embodiments that the inflatable spacer comprises a plurality of inflatable members, each inflatable member can have a corresponding inflation valve 151. For example, as shown in FIG. 4A, the collar 140 houses first and second inflation valves 151a, 151b, each of which controls the flow of the inflation medium to respective inflatable members 200a, 200b via respective media pathways 153a, 153b that can be formed in the central shaft 206. In some embodiments, the inflation valves 151 can be elastomeric slit valves as described above and can be configured to allow respective inflation shafts to be inserted through the valves into the media pathways 153a, 153b for delivering the inflation medium to the inflatable members 200a, 200b. In other embodiments, the inflation valves 151a, 151b can be check valves that are configured to form a releasable connection to respective inflation shafts. For example, respective inflation shafts can be screwed into the inflation valves during delivery and deployment of the prosthetic valve and then unscrewed from the inflation valves and removed from the patient after the prosthetic device 102 is deployed.

In other embodiments, the inflatable spacer of the prosthetic spacer device 102 can be inflated by regulating the flow of blood into the spacers instead of introducing an outside inflation medium into the body. For example, the inflation valves 151 of the inflatable spacer can be one-way valves including check valves, hemostasis valves, and/or other suitable valves configured to regulate the flow of blood into the members.

For example, an inflatable spacer can include a check valve (such as represented by valve 151), for example, housed in the second collar 140, that is configured to allow the flow of blood through the check valve in only one direction into the interior cavity/cavities of the inflatable spacer. The check valve can be configured such that when the pressure at an inflow end of the check valve reaches a minimum threshold (also referred to as the "cracking pressure"), the check valve can move into an open position, allowing blood to pass through the valve and into the interior cavity of the inflatable spacer. The check valve can, for example, be configured to have a cracking pressure substantially equivalent to the blood pressure of a patient where the spacer device is to be implanted. In this manner, the check valve allows the inflatable spacer to fill with blood when the check valve is exposed to blood (e.g., when the prosthetic spacer device 102 is exposed from the sheath 116 of the delivery apparatus 104 in the patient's left atrium).

For implanting the spacer device within the native mitral valve, the one-way valve (e.g., a check valve) can be positioned at or near the upstream end of the spacer (e.g., within collar 140) and can have a cracking pressure substantially equivalent to the blood pressure in the left atrium (e.g., 4-12 mmHg) so that the spacer can be filled with blood flowing from the left atrium to the left ventricle during diastole. Alternatively, the one-way valve (e.g., a check valve) can be positioned at or near the downstream end of the spacer (e.g., within collar 138) and can have a cracking pressure substantially equivalent to the blood pressure in the left ventricle (e.g., 100-140 mmHg) so that the spacer can be filled with blood in the left ventricle flowing toward the left atrium during systole.

In some embodiments, the check valve can be a ball check valve, a diaphragm check valve, a swing check valve, an in-line check valve, or other type of check valve.

In some embodiments, the inflatable spacer can include a structure-creating material and/or gel disposed inside the interior cavity (e.g., the material can fill or partially fill the interior cavity and/or can be an internal coating layer lining an outer layer) such that when a medium (e.g., a fluid such as blood, saline solution, epoxy, gas, etc.) enters the internal cavity of the inflatable spacer the medium contacts the gel and causes the gel to expand and/or solidify within the inflatable spacer cavity.

In other embodiments, the internal cavity of the inflatable spacer can be coated and/or filled with a clotting agent such that when blood enters the internal cavity the inflatable spacer the blood contacts the clotting agent and clots within the inflatable spacer. The internal cavity 146 of the inflatable spacer 132 can, for example, be coated and/or filled with gel foam (e.g., Baxter Gel Foam Plus), a hydrogel, a sponge (e.g., gelatin or other suitable material), thrombin power (e.g., Baxter Thrombin powder), hemostatic matrix (e.g., Baxter FloSeal), spun collagen hemostatic granules, and/or any other suitable material. Using a material that subsequently forms a solid (or at least more rigid) material can help provide additional structural integrity to the inflatable spacer, including resisting changes (deformation) due to the contractions of the heart and fluid flow about the prosthetic spacer device 102.

Referring now to FIG. 3, in some embodiments, the prosthetic spacer device 102 can include a cover 152. In some embodiments, the cover 152 can be disposed over the inflatable spacer 132, the anchors 134, and/or the anchor extension members 142. The cover 152 can be configured to prevent and/or reduce blood-flow through the prosthetic spacer device 102 and/or to promote and/or prevent or slow native tissue ingrowth. In some embodiments, the cover 152 can be a cloth or fabric such as PET, velour, or other suitable fabric. In some embodiments, the cover 152 can comprise an elastic and/or dynamic material that can stretch in one or two directions in order to expand and/or contract as the inflatable spacer size is adjusted, a knit material capable of expansion and/or contraction, or a folded or pleated material.

In other embodiments, in lieu of or in addition to a fabric, the cover 152 can include a coating (e.g., a polymeric coating) that is applied to the prosthetic spacer device 102. In some embodiments, the cover 152 can comprise an elastomeric cloth cover that creates a smooth biocompatible outer surface to promote tissue growth. The elastomeric cloth covering the inflatable spacer 132 can be relatively snug fitting around the spacer when it is in the uninflated state and can stretch and expand as the spacer is inflated. In this manner, the elastomeric cloth provides a smooth outer surface around the spacer without folds or wrinkles if the spacer is underinflated or completely uninflated.

In some embodiments, a first portion of the cover 152 can be configured to promote tissue ingrowth, while a second portion of the cover can be configured to prevent or slow tissue ingrowth. For example, the cover can comprise a material configured to promote tissue ingrowth at a location along the outer surface of the inflatable spacer 132, and a material configured to slow and/or prevent tissue ingrowth at a location near and/or surrounding the anchors 134. In another embodiment, the cover can comprise a material configured to promote tissue ingrowth at a location near and/or surrounding the anchors 134, and a material configured to slow and/or prevent tissue ingrowth along the outer surface of the inflatable spacer 132. This configuration allows ingrowth over the anchors 134 to secure the prosthetic spacer device 102 in place, while preventing or minimizing ingrowth over the central portions of the prosthetic spacer device, mitigating the possibility of mitral stenosis. The prosthetic spacer device 102 is shown without the cover in FIG. 2 and with the cover 152 in FIG. 3, according to one embodiment.

In embodiments wherein the prosthetic spacer device 102 includes a cover 152, the cover 152 can be configured to expand with the inflation of the inflatable spacer 132 and the movement of the anchors 134, clasps 136, and anchor extension members 142 such that the cover 152 remains adjacent to the prosthetic spacer device 102 and does not billow or otherwise become entangled with the components of the prosthetic spacer device.

As mentioned above, the prosthetic spacer device 102 can be releasably coupled to the delivery apparatus 104 by various means. For example, the delivery apparatus can be releasably coupled to the delivery apparatus by one or more of the following: an actuation shaft, inflation shafts, clasp control members, a coupler, and/or a plurality of tethers.

Figure 10:
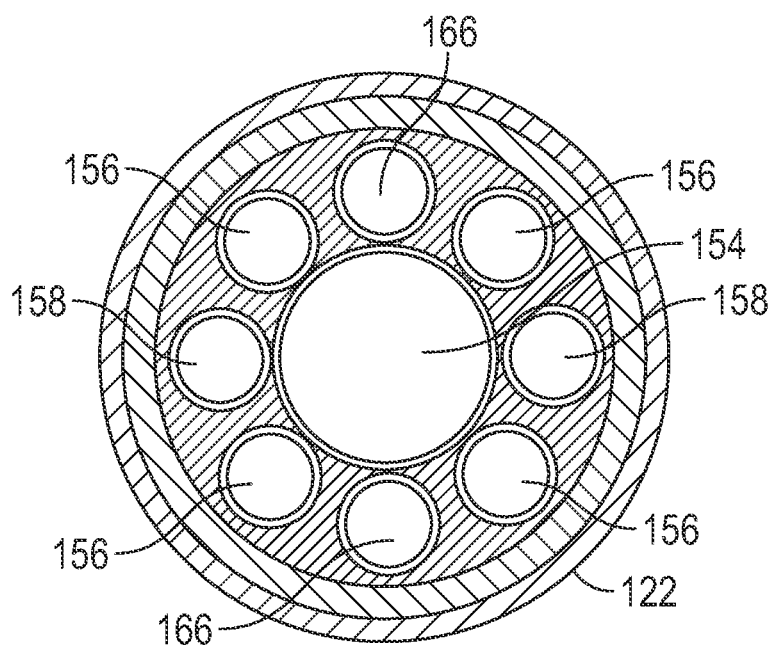
FIG. 10 is a plan view of a shaft of the delivery apparatus of FIG. 1.

Referring now to FIG. 10, the outer shaft 122 of the delivery apparatus 104 can comprise a plurality of axially extending lumina, including an actuation shaft lumen 154, a plurality of control member lumina 156 (e.g., four in the illustrated embodiment), and one or more inflation shaft lumina 158 (e.g., two in the illustrated embodiment). In some embodiments, the outer shaft 122 can comprise more (e.g., six) or less (e.g., two) than four control member lumina 156. In some embodiments, the outer shaft can comprise more (e.g., three) or less (e.g., one) than two inflation shaft lumina 158.

The actuation shaft lumen 154 can be configured to receive the actuation shaft 118, the control member lumina 156 can be configured to receive one or more clasp control members 126, and the inflation shaft lumina 158 can be configured to receive one or more inflation shafts (not shown). The lumina 154, 156, 158 can be configured such that the actuation shaft 118, clasp control members 126, and inflation shafts can be movable (e.g., axially and/or rotationally) relative to the respective lumina 154, 156, 158. In particular embodiments, the lumina 154, 156, 158 can comprise a liner or coating configured to reduce friction within the lumina. For example, the lumina can comprise a liner comprising PTFE.

In some embodiments, as shown in FIGS. 7-8, the actuation shaft 118 of the third catheter 110 can be releasably coupled to the first collar 138 of the prosthetic spacer device 102. For example, the distal end portion 118b of the actuation shaft can comprise external threads configured to releasably engage interior threads of the first collar 138. As such, rotating the actuation shaft 118 in a first direction (e.g., clockwise) relative to the first collar 138 releasably secures the actuation shaft 118 to the first collar 138. Rotating the actuation shaft 118 in a second direction (e.g., counterclockwise) relative to the first collar 138 releases the actuation shaft 118 from the first collar 138.

Referring now to FIG. 7, in some embodiments, the third catheter 110 can be releasably coupled to the second collar 140 of the prosthetic spacer device 102 by coupler 120. The coupler 120 can comprise a plurality of flexible arms 160 and a plurality of stabilizers 162. The coupler 120 can be releasably coupled to the prosthetic spacer device 102 by inserting the stabilizers 162 of the coupler into openings 141 (FIG. 8) of tabs 143 of the second collar 140. The flexible arms 160 can be configured to releasably couple the tabs 143. Additional details regarding the coupler 120 can be found, for example, in U.S. Patent Application Publication No. 2018/0325661 and in U.S. patent application Ser. No. 16/208,264 which are incorporated by reference in their entirety.

In some embodiments where the delivery apparatus includes separate inflation shafts for delivering inflation medium to multiple inflation members, the distal end portions of the inflation shafts can be used in lieu of or in addition to the stabilizer members 162 and the sealing members in the collar 140 that receive the shafts can be used in lieu of or in addition to the openings in the second collar 140.

Figure 9:
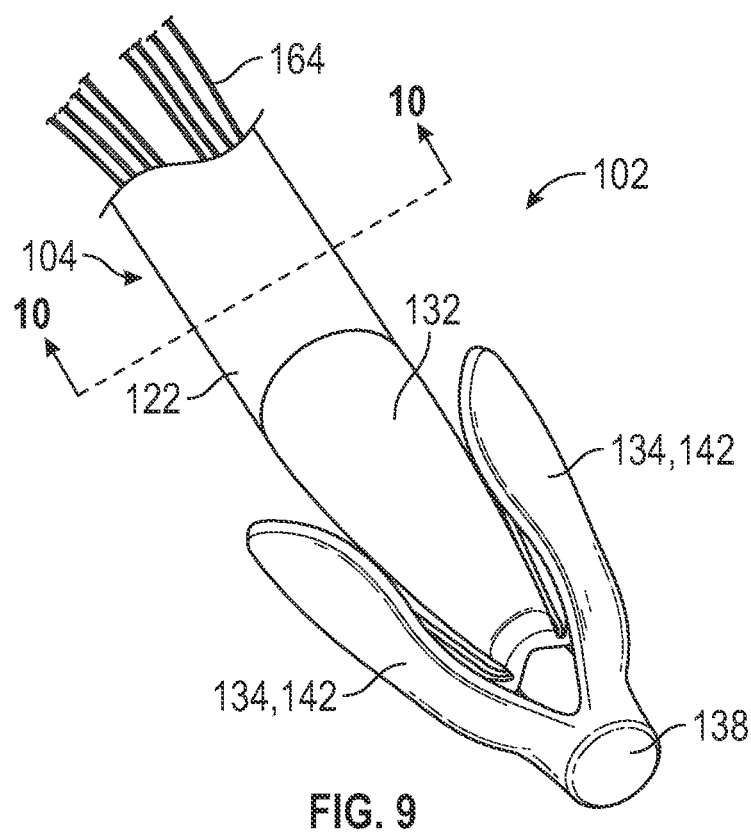
FIG. 9 is a perspective view of a distal end portion of another exemplary delivery assembly showing a prosthetic spacer device releasably coupled to a delivery apparatus.

In other embodiments, as shown in FIG. 9, the prosthetic spacer device 102 can be releasably coupled to the delivery apparatus 104 using a plurality of tethers 164. The tethers 164 can extend through a plurality of tether lumina 166 of the outer shaft (e.g., two in FIG. 10). The tethers 164 can be releasably coupled to the prosthetic spacer device 102. The second collar 140 can have connector members (not shown) for receiving the tethers 164. The connector members can, for example, include openings, eyelets, and/or other suitable means for connecting the tethers 164 to the second collar 140. Tensioning the tethers 164 moves the prosthetic spacer device 102 and the outer shaft 122 toward each other. Slackening the tethers 164 allows the prosthetic spacer device 102 and the outer shaft 122 to be spaced apart from each other.

Figure 11:
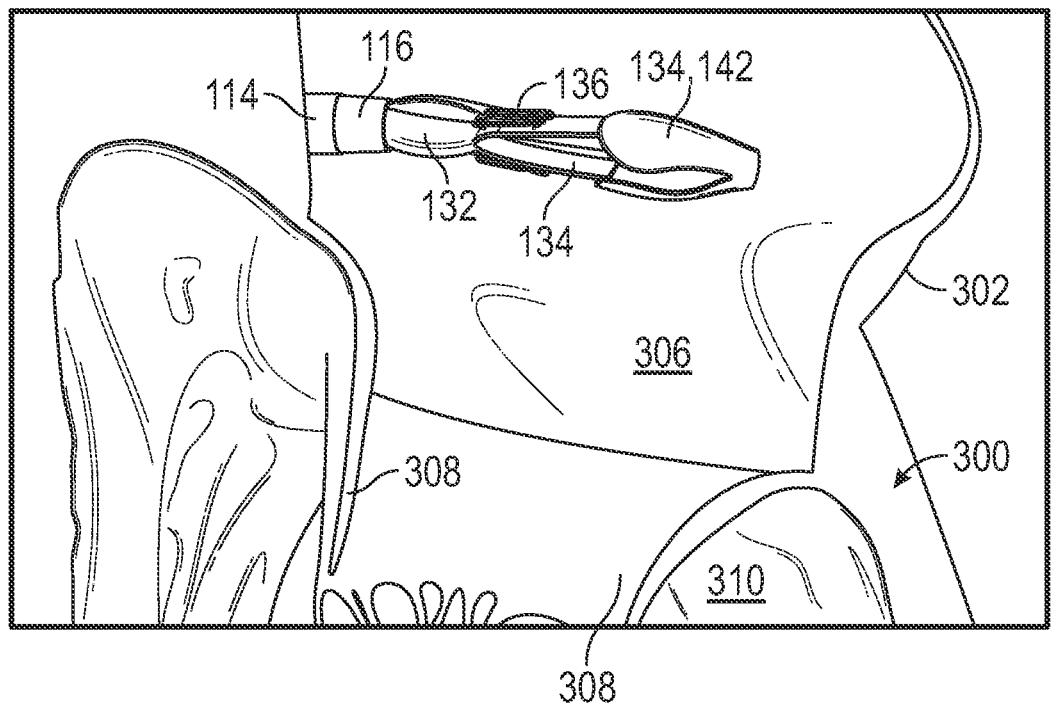
FIGS. 11-15 illustrate an exemplary procedure of the delivery assembly of FIG. 11 being used to repair a native mitral valve of a heart, which is partially shown.

FIGS. 11-17 show the delivery apparatus 104 being used, for example, to implant prosthetic spacer device 102 in native mitral valve 300 of a heart 302 using a transseptal delivery approach. Although not shown, a guide wire can be inserted into the patient's vasculature (e.g., a femoral vain) through an introducer sheath. The guide wire can be advanced through the femoral vein, through the inferior vena cava, into the right atrium, through the interatrial septum 304 (e.g., via the fossa ovalis), and into the left atrium 306. The first sheath 114 of the first catheter 106 can be advanced over the guide wire such that a distal end portion of the first sheath 114 is disposed in the left atrium 306, as shown in FIG. 11.

With the prosthetic spacer device 102 coupled to the third catheter 110 (e.g., as shown in FIG. 7) and configured in a radially compressed, delivery configuration, the prosthetic spacer device 102 can be loaded into the second sheath 116 of the second catheter 108, which retains the prosthetic spacer device 102 in the delivery configuration. In some embodiments, the radially compressed, delivery configuration can be an axially elongate configuration (e.g., similar to the configuration shown in FIG. 11). In other embodiments, the radially compressed delivery configuration can be an axially foreshortened configuration (e.g., similar to the configuration shown in FIG. 9). The second catheter 108 along with the prosthetic spacer device 102 and the third catheter 110 can then be advanced together through the first catheter 106 such that a distal end portion of the second sheath 116 is exposed from the distal end portion of the first sheath 114 and is disposed in the left atrium 306, as shown in FIG. 11.

Referring still to FIG. 11, the prosthetic spacer device 102 can be exposed from the second sheath 114 by distally advancing the outer shaft 122 and the actuation shaft 118 of the third catheter 110 relative to the second sheath 116 and/or retracting the second sheath 116 relative to the outer shaft 122 and the actuation shaft 118, thus forcing the anchors 134 out of the second sheath 116. Once exposed from the second sheath 116, the anchors 134 can be folded by retracting the actuation shaft 118 of the third catheter 110 relative to the outer shaft 122 of the third catheter 110 and/or by advancing the outer shaft 122 relative to the actuation shaft 118, causing the anchors 134 to bend to the configuration shown in FIG. 12. At any point in the procedure, the physician can lock the relative position of the actuation shaft 118 and the outer shaft 122, and thus the position of the anchors 134, by actuating an actuation lock mechanism (not shown) on the handle 124 of the delivery apparatus 104.

The prosthetic spacer device 102 can then be positioned coaxially relative to the native mitral valve 300 by manipulating (e.g., steering and/or bending) the second sheath 116 of the second catheter 108. The prosthetic spacer device 102 can also be rotated relative to the native mitral valve 300 such that the anchors 134 align with native leaflets 308 of the native mitral valve 300.

Figure 12:
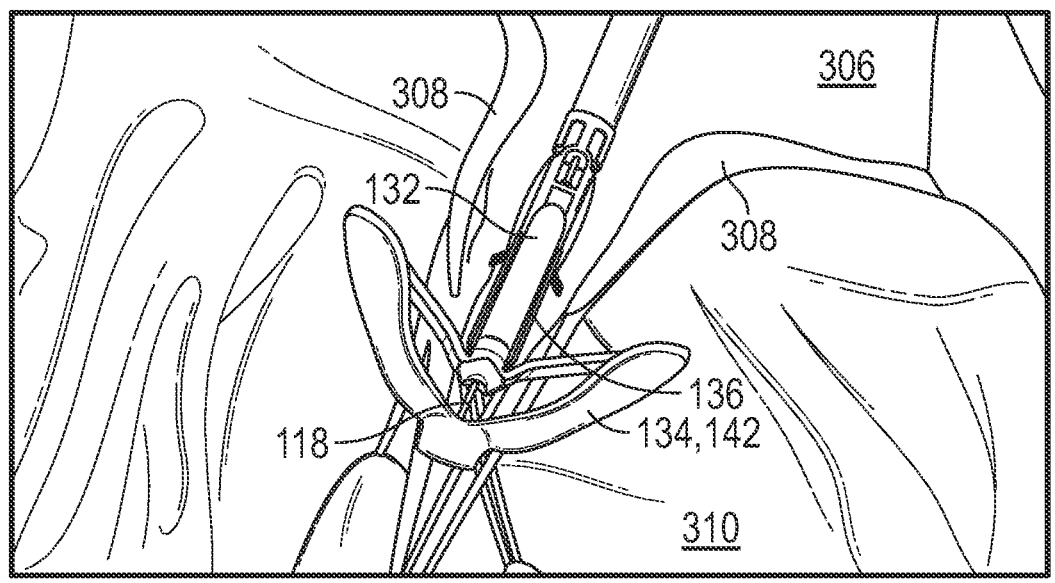

The anchors 134 can then be partially opened (i.e., moved radially outward relative to the uninflated inflatable spacer 132) to the configuration shown in FIG. 12. The prosthetic spacer device 102 can then be advanced through the annulus of the native mitral valve 300 and at least partially into the left ventricle 310. The prosthetic spacer device 102 is then partially retracted such that the anchors 134 are positioned behind the ventricular portions of the native leaflets 308 and the inflatable spacer 132 is disposed on the atrial side of the native leaflets 308.

During the implantation procedure, the inflatable spacer 132 can be initially inflated from the uninflated configuration at various times. For example, in some circumstances, the inflatable spacer 132 can be inflated after the prosthetic spacer device 102 is exposed from the second sheath 116 and prior to coupling the anchors 134 of the prosthetic spacer device 102 to the native leaflets 308 and/or positioning the inflatable spacer 132 between the native leaflets 308. In other circumstances, the inflatable spacer 132 can be inflated after the prosthetic spacer device 102 is exposed from the second sheath 116 and after coupling the anchors 134 of the prosthetic spacer device 102 to the native leaflets 308 and/or positioning the inflatable spacer 132 between the native leaflets 308.

Referring now to FIG. 13, the native leaflets 308 can be secured relative to the anchors 134 by capturing the native leaflets 308 with the clasps 136. The native leaflets 308 can be captured simultaneously or separately. For example, FIG. 13 shows separate leaflet capture. Additional details regarding the implantation of prosthetic spacer devices can be found, for example, in U.S. Patent Application Publication No. 2018/0325661.

Figure 14:
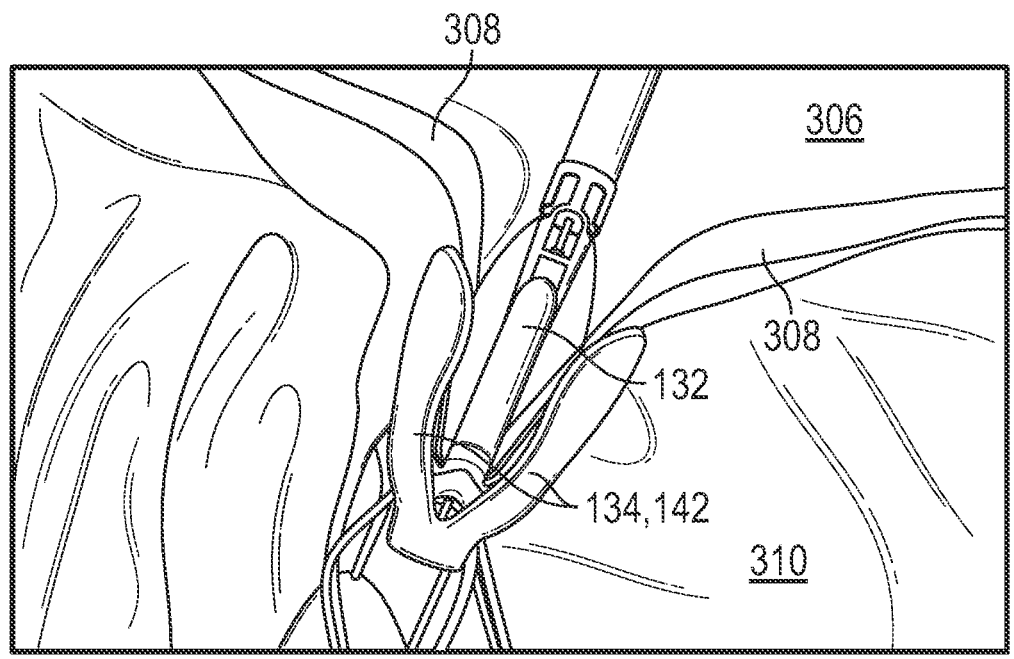

Once a clasp 136 is closed, a physician can re-open the clasp 136 to adjust the positioning of the clasp. As the clasps re-open, the clasps move radially inward toward the inflatable spacer 132 until the clasps 136 contact the inflatable spacer 132. With both of the native leaflets 308 secured within the clasps 136, the anchors 134 (and thus the native leaflets 308) can be pulled radially inward against the inflatable spacer 132, as shown in FIG. 14. The inflatable spacer 132 can then be inflated. The physician can then observe the positioning and/or reduction in regurgitation.

The interior and/or exterior surfaces of the prosthetic spacer device 102 can include additional features. For example, a portion of the prosthetic spacer device 102, such as a central portion, can house or support a radiopaque (fluoroscopic) or echogenic marker, which can be used to help locate and position the prosthetic spacer device 102 during implantation. When the inflatable spacer 132 is inflated asymmetrically, the marker can be used to confirm that the inflatable spacer is positioned in the desired configuration.

For purposes of description, FIGS. 11-14 show prosthetic spacer device 102 comprising a single inflatable spacer 132, however, the method of implantation described herein can have substantially the same steps in embodiments wherein prosthetic spacer device 102 comprises a plurality of inflatable members.

Figure 16:
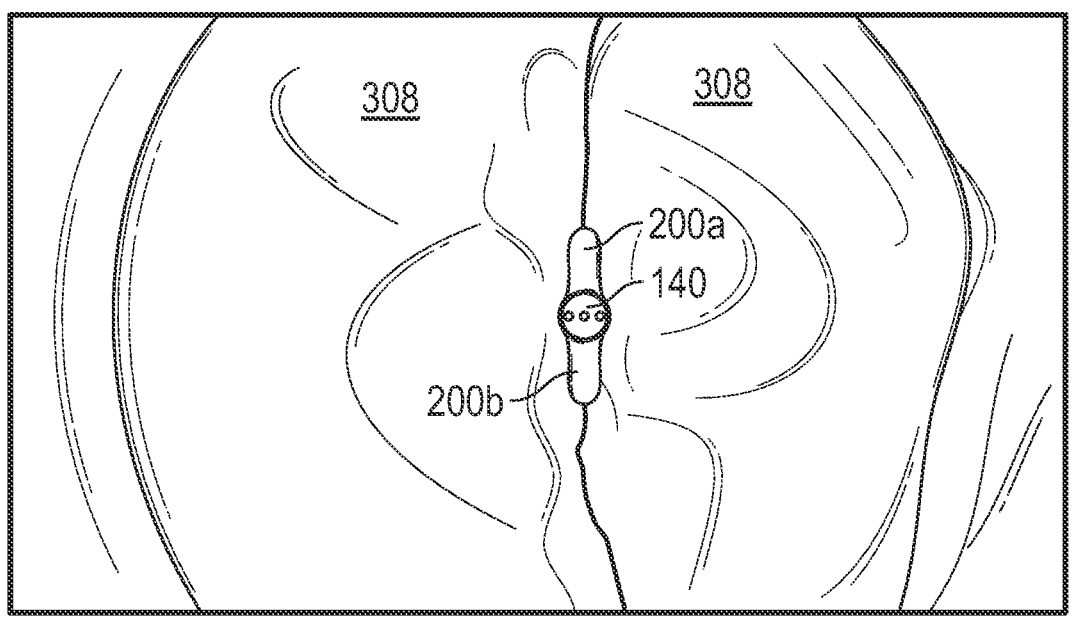
FIG. 16 is a plan view of the prosthetic spacer device of FIG. 5A implanted within a native mitral valve.

In embodiments having a plurality of inflatable members, a physician can inflate or deflate each inflatable member based on the anatomical considerations of the patient. In embodiments with a plurality of inflatable members (e.g., the first and second inflatable members 200a, 200b), the physician can begin by partially or fully inflating one of the inflatable members (e.g., the first inflatable member 200a). The physician can then monitor the patient's mitral regurgitation. If further sealing of the mitral valve is needed, the physician can, for example, further inflate the first inflatable member 200a and/or inflate the second inflatable member 200b such that both members are at least partially inflated (e.g., as shown in FIG. 16).

If the positioning of the prosthetic spacer device and/or the reduction in regurgitation is not as desired, the physician can adjust the location of the prosthetic spacer device 102 within the mitral valve by re-opening the anchors 134 and/or clasps 136 and releasing the native leaflets 308 and removing and/or repositioning the prosthetic spacer device 102. Additionally, the physician can inflate/deflate the inflatable members to adjust the level of mitral regurgitation and/or other considerations.

Figure 15:
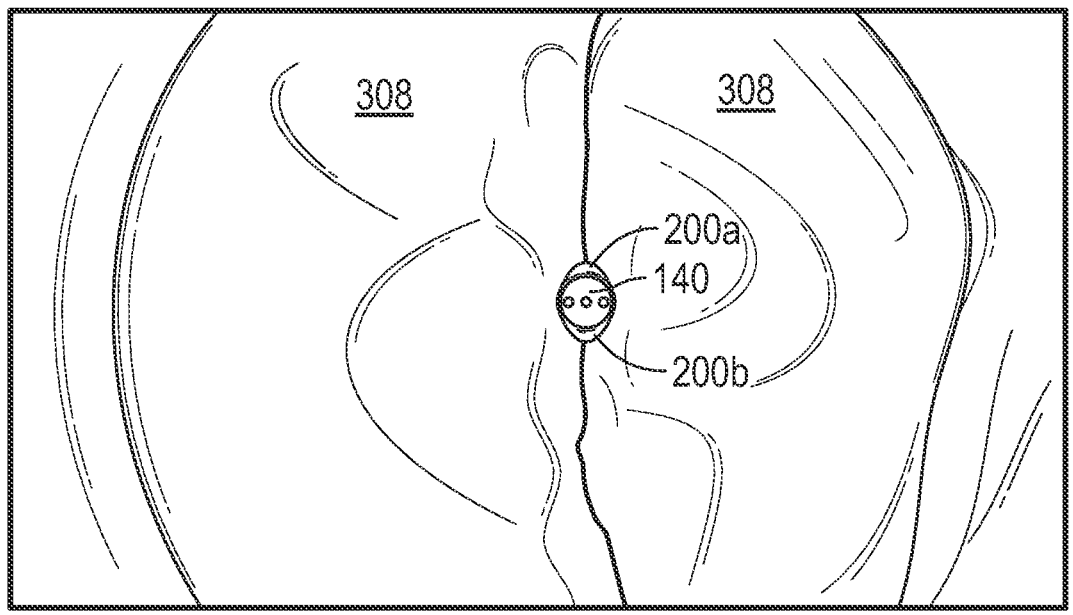
Figure 17:
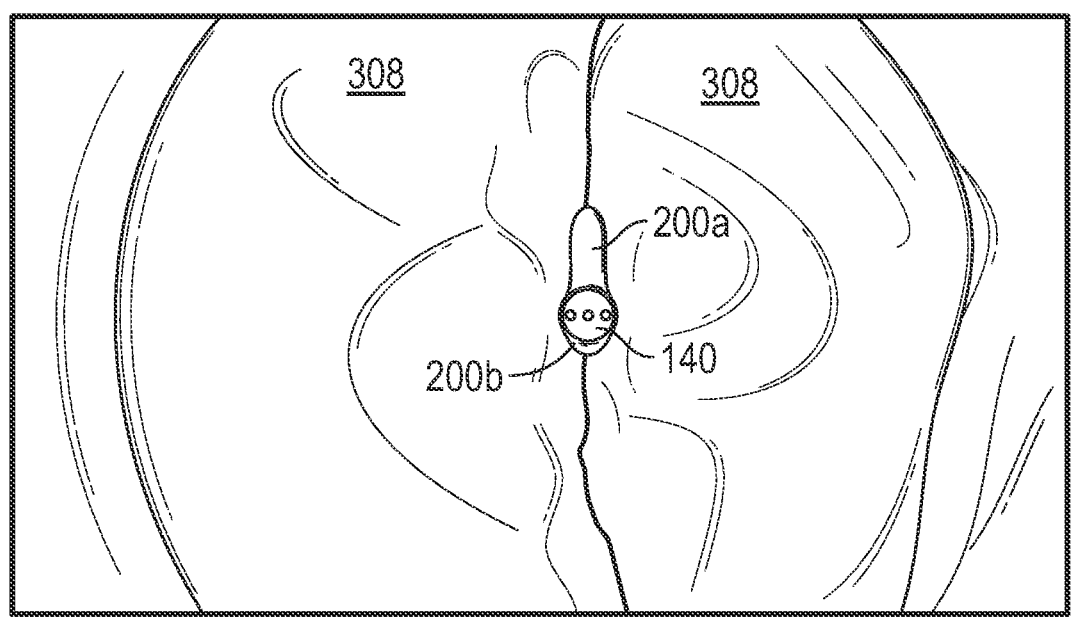
FIG. 17 is a plan view of the prosthetic spacer device of FIG. 4A implanted within a native mitral valve.

The physician can then reevaluate the positioning and/or functionality of the prosthetic spacer device and, if desired, make additional adjustments. The prosthetic spacer device can be adjusted into various configurations. For example, FIG. 15 shows an embodiment of the prosthetic spacer device 102 having two inflatable members 200 implanted in a symmetrical configuration with both first and second inflatable members 200a, 200b in the uninflated configuration. FIG. 16 shows the same embodiment in a symmetrical configuration with both first and second inflatable members 200a, 200b in the fully inflated configuration, and FIG. 17 shows the same embodiment in an asymmetrical configuration with first inflatable member 200a in an inflated configuration and second inflatable member 200b in an uninflated configuration. Any combination of uninflated, partially inflated, and/or fully inflated configurations for the inflatable spacers can be used.

In embodiments wherein the prosthetic spacer device 102 is releasably coupled to the delivery apparatus using a coupler 120 (see e.g., FIGS. 7-8), once the actuation shaft 118 has been retracted proximally the stabilizer members 162 can be withdrawn from the guide openings in the second collar, thereby releasing the prosthetic spacer device 102 from the delivery apparatus 104. The clasp control members 126 and inflation shafts can then be retracted proximally into the lumina 156, 158 of the outer shaft 122, and the outer shaft together with the actuation shaft 118 can be retracted proximally through the first and second catheters and removed from the patient's body.

In embodiments wherein the prosthetic spacer device is coupled to the delivery apparatus using a plurality of tethers 164, the delivery apparatus can be implanted in a manner similar to that described above and as shown in FIGS. 11-15. However, once positioned, the physician can slacken the tethers 164, clasp control members 126, and inflation shafts such that the outer shaft 122 can be spaced from the proximal end portion of the prosthetic spacer device 102. In this manner, the prosthetic spacer device can be partially released from the delivery apparatus 104, but the tethers 164, clasp control members 126, and inflation shafts remain coupled to the prosthetic spacer device 102. Due to the flexibility and slack of the tethers, the clasp control members, and the inflation shafts, the prosthetic spacer device can move and/or function as if it were fully released from the delivery apparatus. As a result, the partially released configuration can, for example, allow the physician to better evaluate the functionality and/or positioning of the prosthetic spacer device 102 prior to fully releasing the device and can reposition and/or remove the device, or can deflate/inflate the inflatable spacer 132 as needed to improve functionality. This is because the outer shaft 122 and/or the actuation shaft 118 are relatively more rigid than the clasp control members 126, the tethers 164, and the inflation shafts, and can thus alter the position and/or hemodynamics of the prosthetic spacer device 102 compared to when the prosthetic spacer device 102 is partially or fully released from the delivery apparatus 104.

If the physician would like to adjust the positioning of the prosthetic spacer device 102, the tethers 164 can be tightened and the distal end portion 122b of the outer shaft 122 can be advanced distally over the tethers 164 such that it abuts the proximal end portion of the prosthetic spacer device. The actuation shaft 118 can be advanced distally through the central lumen of the outer shaft 122 and reconnected to the first collar 138. The prosthetic spacer device 102 can then be moved relative to the native leaflets by actuating the actuation shaft 118 and/or the clasp control members 126 to manipulate the anchors 134 and/or the clasps 136 respectively. The prosthetic spacer device can then be moved relative to the native leaflets by actuating the actuation shaft 118 and/or the clasps 134, respectively. The physician can then reevaluate the positioning and/or functionality of the prosthetic spacer device and, if desired, make additional adjustments.

Once the desired positioning and/or reduction in regurgitation is achieved, the physician can release the prosthetic spacer device 102 from the delivery apparatus 104. The clasps 136 can be released from the delivery apparatus 104 by releasing the clasp control members 126 and unthreading the clasp control members 126 from the openings of the clasps. The first collar 138 of the prosthetic spacer device 102 can be released from the delivery apparatus 104 by rotating the knob 128 in the second direction (e.g. counter-clockwise) such that the actuation shaft 118 retracts proximally relative to the first collar 138. The actuation shaft 118 can then be retracted proximally through the prosthetic spacer device 102. The second collar 140 of the prosthetic spacer device can then be released from the delivery apparatus by retracting the actuation shaft 118 proximally relative to the second collar 140.

The clasp control members, inflation shafts, and tethers can then be retracted proximally into the lumina 156, 158, 166 of the outer shaft 122, and the outer shaft together with the actuation shaft 116 can be retracted proximally through the first and second catheters and removed from the patient's body.

With the prosthetic spacer device implanted at the A2/P2 position and the delivery apparatus removed, the native mitral valve can, in some embodiments, comprise a double orifice during ventricular diastole. During ventricular systole, the native leaflets 308 can coapt together and/or against the prosthetic spacer device to prevent or reduce mitral regurgitation (see e.g., FIGS. 15-17). As shown in FIGS. 15-17, different inflation configurations of the prosthetic spacer device create different surfaces against which the native leaflets 308 can coapt.

In some embodiments, the anchors can move radially outward relative to the inflatable spacer to a partially open configuration during ventricular diastole such that the native mitral valve has a single continuous orifice. Configuring the prosthetic spacer device in this manner allows the native leaflets 308 to move naturally. This can, for example, promote antegrade blood flow during ventricular diastole while still reducing or preventing retrograde blood flow during ventricular systole. It can also reduce or prevent native tissue damage to the native leaflets 308.

In other embodiments, any of the prosthetic spacer devices disclosed herein can include an inflatable spacer (having one or more inflatable members) and a frame configured to be mounted on only one native valve leaflet, such as one of the native mitral valve leaflets. In such embodiments, the frame can comprise one anchor, and optionally, one clasp, for mounting on one native leaflet. When so mounted, the prosthetic spacer device can move with the native leaflet on which it is mounted during the cardiac cycle, while another native leaflet can coapt against the prosthetic spacer device In addition, a prosthetic spacer device need not be implanted directly on one or more of the native leaflets and instead can comprise any suitable anchor configured to retain an inflatable spacer between native leaflets of a heart valve. For example, the anchor can comprise a structure configured to engage a portion of a heart wall, such as a portion of the left ventricle wall, or a portion of an annulus of a native heart valve. For example, a prosthetic spacer device can comprise an inflatable spacer mounted on an anchor in the form of a shaft, which is configured to engage a heart wall. In a specific implementation, the inflatable spacer is mounted on an upper end of the shaft and the lower end of the shaft is configured to anchor against a wall of the left ventricle, such as at the apex of the heart. In another example, the inflatable spacer can include barbs or other securing means to attach to the native leaflet surface. In another example, a frame is configured to engage the inner wall of the left atrium and support an inflatable spacer in the native mitral valve downstream of the frame. Further details about anchors for anchoring against different portions of the heart and which can be implemented in a prosthetic spacer device are disclosed in U.S. Pat. Nos. 8,758,432 and 8,968,395, which are incorporated herein by reference. In all such examples, the inflatable spacer and/or inflatable members can be inflated and/or deflated in the manner described above.

The repair devices described herein (e.g., prosthetic spacer device 102) have been described in the context of repairing a native mitral valve. However, it should be understood that the repair devices can be used to repair other native heart valves, or artificial heart valves or artificial heart valve components (e.g., artificial leaflets), including using various transcatheter techniques (e.g., transatrial, transventricular, etc.). The prosthetic spacer device 102 can, for example, be used to reduce or improve valvular regurgitation by improving coaptation between heart valve leaflets. In the case of artificial heart valve leaflets, after implantation of such leaflets, over time, the leaflet may exhibit changed mechanical or structural properties (e.g., sagging), or the shape of the heart or its components may change, such that the heart valve leaflets (e.g., an artificial leaflet and one or more natural leaflets, or multiple artificial leaflets, optionally with a natural leaflet) may no longer coapt to a desired degree. The disclosed repair devices can be implanted to reposition an artificial leaflet to improve coaptation with one or more other leaflets.

Although a transseptal delivery technique is described in detail above, any of various other delivery techniques can be used to deliver a positioning device through a patient's vasculature. In a transfemoral procedure, the delivery apparatus can be inserted through a femoral artery and the aorta to the heart in a retrograde direction. Alternatively, the delivery apparatus can be inserted through a femoral vein and the vena cava to the right side of the heart in an antegrade direction, such as for implanting a positioning device on one of the leaflets of the tricuspid valve. In a transventricular procedure, the delivery apparatus can be inserted through a surgical incision made in the chest and at a location on the left or right ventricle to access valves on the left and right sides of the heart. For example, the delivery apparatus can be inserted through an incision made on the bare spot on the lower anterior ventricle wall to access the left ventricle. Similarly, the delivery apparatus can be inserted through a surgical incision on the wall of the right ventricle to access the pulmonary or tricuspid valves. In a transatrial procedure, the delivery apparatus can be inserted through a surgical incision made in the wall of the left or right atrium to access the native valves on the left or right sides, respectively, of the heart. In a transaortic procedure, the delivery apparatus can be inserted through a surgical incision made in the ascending aorta and advanced toward the heart. Further details of delivery techniques for accessing the native valves of the heart are disclosed in U.S. Pat. No. 9,414,918, which is incorporated herein by reference.

Figure 18:
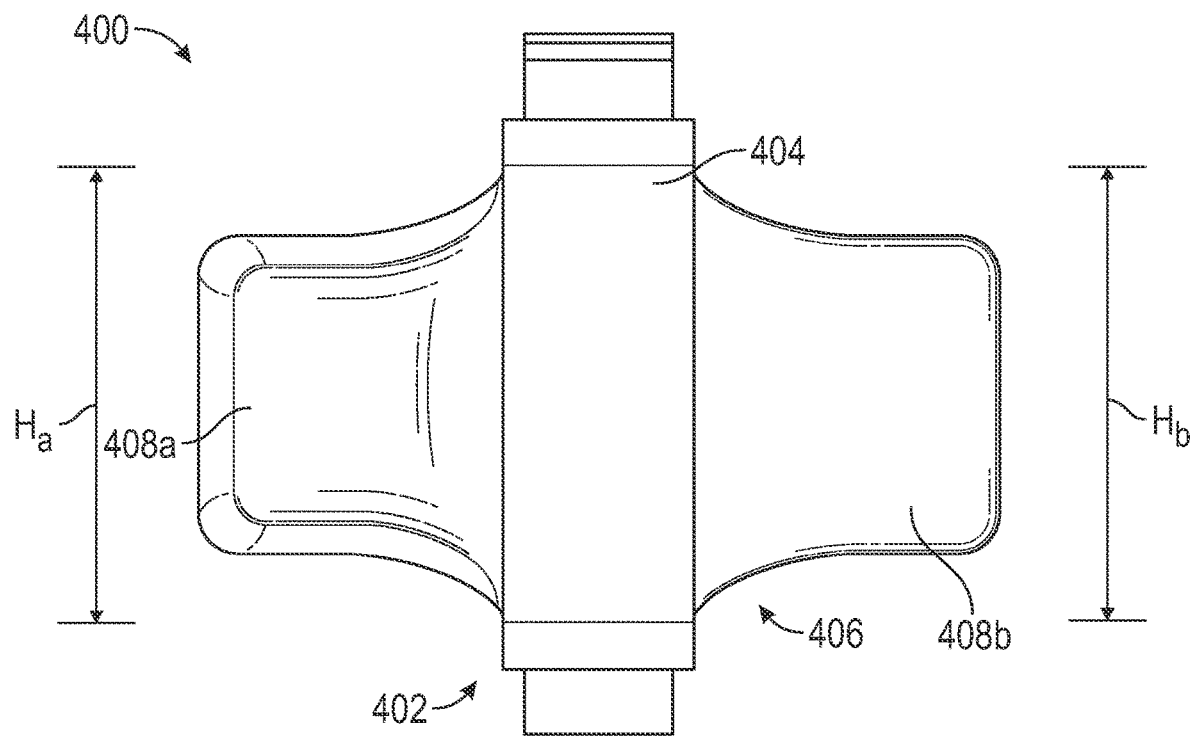
FIG. 18 is a side elevation view of an embodiment of a prosthetic spacer device in an asymmetrically inflated configuration.
Figure 19:
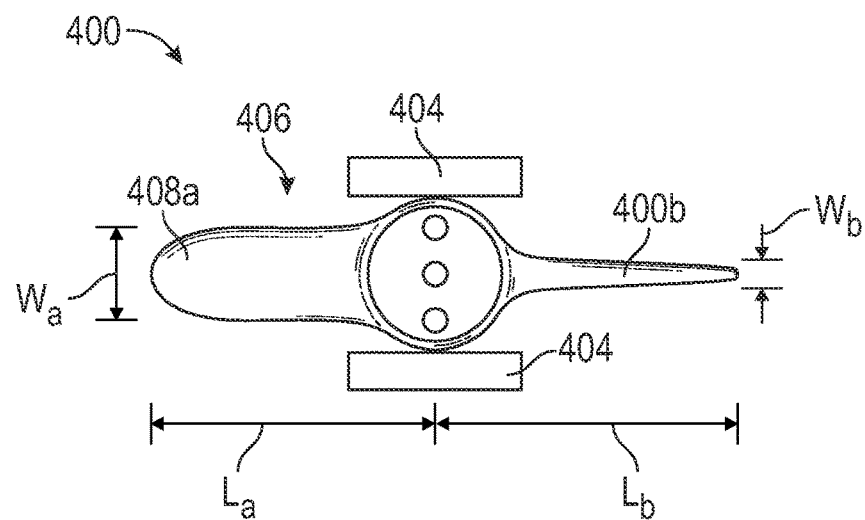
FIG. 19 is a plan view of the prosthetic spacer device of FIG. 18.

FIGS. 18-19 illustrate an exemplary prosthetic spacer device 400. The prosthetic spacer device 400 is substantially similar to embodiment 200, except when in an uninflated configuration. The prosthetic spacer device 400 comprises a frame 402, anchors 404, and inflatable spacer 406 having a plurality of inflatable members 408 (e.g., two in the illustrated embodiment 408a, 408b).

As shown in the illustrated embodiment, the inflatable members 408a, 408b can have respective lengths $L_a$, $L_b$, widths $W_a$, $W_b$, and heights $H_a$, $H_b$. The inflatable members 408a, 408b can be configured such that one or more of the length, width, and/or height dimensions of the inflatable members are fixed such that the inflatable member does not vary (at least not substantially) in the pre-determined dimensions when the inflatable members are moved between the inflated and uninflated configurations.

The inflatable members 408a, 408b can be configured such that one or more of the length, width, and/or height dimensions of the inflatable members are variable such that the inflatable members vary when the inflatable members are moved between the inflated and uninflated configurations. For example, in the embodiment of FIGS. 18-19, the inflatable members 408a, 408b are configured such that the length and height dimensions of the inflatable members do not vary and the width dimension does vary as the inflatable members are moved between the inflated configuration (e.g., the inflatable member 408a) and the uninflated configuration (e.g., the inflatable member 408b). In some embodiments, the pre-determined fixed dimension of both inflatable members can be the same dimension (e.g., $L_a$ and $L_b$) and/or the same size (e.g., $L_a = L_b$). In other embodiments, the pre-determined fixed dimensions of the inflatable spacers can be different dimensions (e.g., $L_a$ and $W_a$) and/or different sizes (e.g., $L_a$ $L_b$).

The inflatable members 408a, 408b can be partially inflated, fully inflated, and/or deflated independently of one another. In some embodiments, each of the inflatable members 200 can be deflated and/or partially or fully inflated independently of one another to create various symmetrical or asymmetrical configurations. FIGS. 18-19 show an exemplary asymmetrical configuration that is achieved by inflating the first inflatable member 408a to an inflated configuration and maintaining the second inflatable member 408b in an uninflated configuration. In the illustrated embodiment, inflating an inflatable member 408a, 408b increases the width $W_a$ so as to occupy more space between opposing leaflets of a regurgitant valve, while the height $H_a$ and the length $L_a$ remain constant or substantially constant upon inflation.

In other respects, (e.g., inflation and/or deflation, implantation, and repositioning) prosthetic spacer device 400 can be configured to function substantially similarly to prosthetic spacer device 200.

The features described herein with regard to any example can be combined with other features described in any one or more of the other examples, unless otherwise stated.

In view of the many possible embodiments to which the principles of the disclosed invention may be applied, it should be recognized that the illustrated embodiments are only preferred examples of the invention and should not be taken as limiting the scope of the claims. Rather, the scope of the claimed subject matter is defined by the following claims and their equivalents.

The invention claimed is:

1. A method for improving coaptation of native heart valve leaflets comprising:
   advancing a delivery apparatus and an implantable prosthetic device into a body of a patient, the implantable prosthetic device comprising an adjustable spacer;
   positioning the adjustable spacer between the native heart valve leaflets such that the adjustable spacer is offset from an area of regurgitation;
   adjusting a size of the adjustable spacer while the adjustable spacer is disposed between the native heart valve leaflets so that the adjustable spacer assumes an asymmetric configuration such that the adjustable spacer blocks the area of regurgitation;
   wherein the adjustable spacer has a first side adjustable in size and a second side adjustable in size; and
   wherein the first side is adjusted in size independently of the second side.

2. The method of claim 1, wherein the asymmetric configuration is asymmetric with respect to a central longitudinal axis of the adjustable spacer that extends from an upstream end to a downstream end of the adjustable spacer.

3. The method of claim 1, wherein the asymmetric configuration is asymmetric with respect to a lateral axis of the adjustable spacer.

4. The method of claim 1, wherein the first side and the second side are different sizes or shapes in an expanded configuration.

5. The method of claim 1, wherein the size of the adjustable spacer is adjusted by inflating the adjustable spacer with an inflation medium.

6. A method for improving coaptation of native heart valve leaflets comprising:
   advancing a delivery apparatus and an implantable prosthetic device into a body of a patient, the implantable prosthetic device comprising an adjustable spacer;
   positioning the adjustable spacer between the native heart valve leaflets such that the adjustable spacer is offset from an area of regurgitation;
   wherein the adjustable spacer is offset toward an A1/P1 location when the area of regurgitation is an A2/P2 location; and
   adjusting a size of the adjustable spacer while the adjustable spacer is disposed between the native heart valve leaflets so that the adjustable spacer assumes an asymmetric configuration such that the adjustable spacer blocks the area of regurgitation.

* * * * *